US009566302B2

(12) United States Patent
Applewhite et al.

(10) Patent No.: US 9,566,302 B2
(45) Date of Patent: Feb. 14, 2017

(54) COMPOSITION COMPRISING MIXED METAL COMPOUNDS AND XANTHAN GUM

(75) Inventors: Richard Jonathan Applewhite, Cheshire (GB); Maurice Sydney Newton, Sandbach (GB); Alexis John Toft, Warrington (GB)

(73) Assignee: OPKO IRELAND GLOBAL HOLDINGS, LTD., Grand Cayman (KY)

( * ) Notice: Subject to any disclaimer, the term of this patent is extended or adjusted under 35 U.S.C. 154(b) by 60 days.

(21) Appl. No.: 13/576,426

(22) PCT Filed: Feb. 3, 2011
(Under 37 CFR 1.47)

(86) PCT No.: PCT/GB2011/050185
§ 371 (c)(1),
(2), (4) Date: Mar. 13, 2013

(87) PCT Pub. No.: WO2011/095812
PCT Pub. Date: Aug. 11, 2011

(65) Prior Publication Data
US 2013/0323325 A1   Dec. 5, 2013

(30) Foreign Application Priority Data
Feb. 4, 2010 (GB) .................. 1001779.6

(51) Int. Cl.
| *A61K 33/26* | (2006.01) |
| *A61K 9/10* | (2006.01) |
| *A61K 33/06* | (2006.01) |
| *A61K 33/24* | (2006.01) |
| *A61K 33/30* | (2006.01) |
| *A61K 47/32* | (2006.01) |
| *A61K 47/36* | (2006.01) |
| *A61K 47/38* | (2006.01) |

(52) U.S. Cl.
CPC ............... *A61K 33/26* (2013.01); *A61K 9/10* (2013.01); *A61K 33/06* (2013.01); *A61K 33/24* (2013.01); *A61K 33/30* (2013.01); *A61K 47/32* (2013.01); *A61K 47/36* (2013.01); *A61K 47/38* (2013.01)

(58) Field of Classification Search
None
See application file for complete search history.

(56) References Cited

U.S. PATENT DOCUMENTS

| 2,222,924 A | 11/1940 | Weiss |
| 2,812,344 A | 11/1957 | Oroshnik |
| 3,101,270 A | 8/1963 | Evans et al. |
| 3,395,211 A | 7/1968 | Wielich |
| 3,650,704 A | 3/1972 | Kumura et al. |
| 3,743,098 A | 7/1973 | Martinez |
| 3,796,792 A | 3/1974 | Miyata et al. |
| 3,879,523 A | 4/1975 | Miyata et al. |
| 3,984,392 A | 10/1976 | van der Veen et al. |
| 4,192,900 A | 3/1980 | Cheng |
| 4,254,099 A | 3/1981 | Asmussen et al. |
| 4,351,814 A | 9/1982 | Miyata et al. |
| 4,370,280 A | 1/1983 | Oediger et al. |
| 4,415,555 A | 11/1983 | Anabuki et al. |
| 4,458,026 A | 7/1984 | Reichle |
| 4,514,389 A | 4/1985 | Miyata |
| 4,566,986 A | 1/1986 | Waldmann |
| 4,582,705 A | 4/1986 | Primes et al. |
| 4,609,543 A | 9/1986 | Morris et al. |
| 4,629,626 A | 12/1986 | Miyata et al. |
| 4,661,330 A | 4/1987 | Chane-Ching et al. |
| 4,689,219 A | 8/1987 | Sugden |
| 4,735,629 A | 4/1988 | Glemser et al. |
| 4,786,510 A | 11/1988 | Nakel et al. |
| 4,801,454 A | 1/1989 | Coveney |
| 4,970,079 A | 11/1990 | Hem et al. |
| 4,994,283 A | 2/1991 | Mehansho et al. |
| 5,002,747 A | 3/1991 | Le Loarer |
| 5,085,869 A | 2/1992 | Olthoff et al. |
| 5,112,604 A | 5/1992 | Beaurline et al. |
| 5,153,156 A | 10/1992 | Schutz et al. |
| 5,173,284 A | 12/1992 | Moisset et al. |

(Continued)

FOREIGN PATENT DOCUMENTS

| CA | 1198674 | 12/1985 |
| DE | 3346943 | 7/1985 |

(Continued)

OTHER PUBLICATIONS

Kebler et., "Dynamic changes in serum phosphorus levels in diabetic ketoacidoses" The American Journal of Medicine, (1985), vol. 79, Issue 5, pp. 571-576.*
McIntyre et al., "Iron-Magnesium Hydroxycarbonate (Fermagate): A Novel Non-Calcium-Containing Phosphate Binder for the Treatment of Hyperphosphatemia in Chronic Hemodialysis Patients" Clin. J. Am. Soc. Nephrol. (Published online on Jan. 2009), vol. 4, pp. 401-409.*
Abramowitz et al., Serum alkaline phosphatase and phosphate and risk of mortality and hospitalization, Clin. J. Am. Soc. Nephrol., 1:1064-71 (2010).
Adachi-Pagano et al., Synthesis of Al-rich hydrotalcite-like compounds by using the urea hydrolysis reaction-control of size and morphology, J. Mater. Chem., 13(8):1988-93 (2003).
Adams et al., Formulation of a sterile surgical lubricant, J. Pharm. Pharmacol., 24 Suppl:178P (1972).
Albaaj et al., Hyperphosphataemia in renal failure: causes, consequences and current management, Drugs, 63(6):577-96 (2003).

(Continued)

*Primary Examiner* — Abigail Fisher
*Assistant Examiner* — Daniel Branson
(74) *Attorney, Agent, or Firm* — Marshall, Gerstein & Borun LLP

(57) ABSTRACT

The present invention provides a composition comprising (i) a mixed metal compound containing at least one trivalent metal selected from iron (lll) and aluminum and at least one divalent metal selected from of magnesium, iron, zinc, calcium, lanthanum and cerium, (ii) xanthan gum (iii) at least one of (a) polyvinyl pyrrolidone (b) locust bean gum (c) methyl cellulose wherein the composition has been irradiated with ionizing radiation in an amount of at least 4 kGy.

26 Claims, 1 Drawing Sheet

(56) References Cited

U.S. PATENT DOCUMENTS

Figure 1:
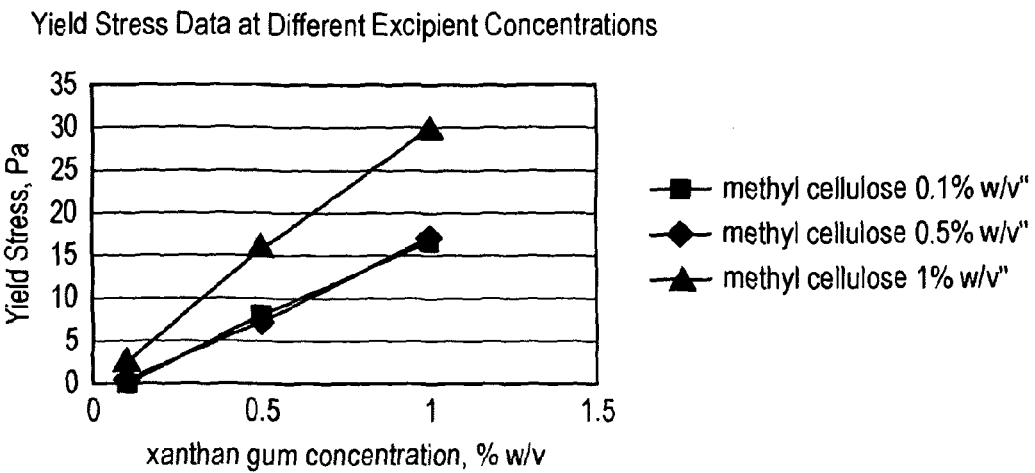

| | | |
|---|---|---|
| 5,185,093 A | 2/1993 | Ichikawa et al. |
| 5,213,794 A | 5/1993 | Fritsch et al. |
| 5,246,899 A | 9/1993 | Bhattacharyya |
| 5,273,767 A | 12/1993 | Burgum |
| 5,300,302 A | 4/1994 | Tachon et al. |
| 5,506,248 A | 4/1996 | Nikfar et al. |
| 5,514,281 A | 5/1996 | Boos et al. |
| 5,525,305 A | 6/1996 | Minekus et al. |
| 5,571,336 A | 11/1996 | Wurzburger et al. |
| 5,651,997 A | 7/1997 | Makino et al. |
| 5,654,011 A | 8/1997 | Jackson et al. |
| 5,656,080 A | 8/1997 | Staniforth et al. |
| 5,817,340 A | 10/1998 | Roche et al. |
| 5,846,426 A | 12/1998 | Boos et al. |
| 5,968,976 A | 10/1999 | Murrer et al. |
| 6,028,023 A | 2/2000 | Vierheilig |
| 6,039,981 A | 3/2000 | Woo et al. |
| 6,103,126 A | 8/2000 | Boos et al. |
| 6,174,442 B1 | 1/2001 | Geisser et al. |
| 6,287,596 B1 | 9/2001 | Murakami et al. |
| 6,448,323 B1 | 9/2002 | Jordan et al. |
| 6,576,255 B1 | 6/2003 | Petereit et al. |
| 6,576,665 B2 | 6/2003 | Dennett, Jr. et al. |
| 6,596,311 B1 | 7/2003 | Dobetti |
| 6,696,087 B2 | 2/2004 | Matsuda et al. |
| 6,720,005 B1 | 4/2004 | Ayres |
| 6,733,780 B1 | 5/2004 | Tyler et al. |
| 6,749,864 B2 | 6/2004 | Makino et al. |
| 6,790,895 B2 | 9/2004 | Stelandre et al. |
| 6,794,367 B1 | 9/2004 | Tanida et al. |
| 6,926,912 B1 | 8/2005 | Roberts et al. |
| 7,259,192 B2 | 8/2007 | Liu et al. |
| 7,300,670 B2 | 11/2007 | Venus et al. |
| 7,799,351 B2 | 9/2010 | Roberts et al. |
| 2002/0122786 A1 | 9/2002 | Matsuda et al. |
| 2003/0150249 A1 | 8/2003 | Gillman et al. |
| 2003/0185886 A1 | 10/2003 | Lee et al. |
| 2004/0022872 A1 | 2/2004 | Sofue et al. |
| 2004/0105896 A1 | 6/2004 | Roberts et al. |
| 2004/0247696 A1 | 12/2004 | Antelman |
| 2005/0260271 A1 | 11/2005 | Bringley |
| 2005/0266071 A1 | 12/2005 | Olmstead et al. |
| 2006/0177415 A1 | 8/2006 | Burke |
| 2007/0107637 A1 | 5/2007 | Gambin et al. |
| 2008/0187602 A1 | 8/2008 | Ferdinando et al. |
| 2009/0162658 A1 | 6/2009 | Wolk et al. |
| 2009/0175959 A1 | 7/2009 | Bando et al. |
| 2009/0317459 A1 | 12/2009 | Pennel et al. |
| 2010/0215770 A1 | 8/2010 | Newton et al. |
| 2011/0014301 A1 | 1/2011 | Roberts et al. |
| 2012/0093943 A1 | 4/2012 | Newton et al. |
| 2012/0201864 A1 | 8/2012 | Applewhite et al. |

FOREIGN PATENT DOCUMENTS

| | | |
|---|---|---|
| DE | 3402878 | 8/1985 |
| DE | 3801382 | 8/1989 |
| EP | 0134936 | 3/1985 |
| EP | 0150792 | 8/1985 |
| EP | 0368420 | 5/1990 |
| EP | 0577294 | 1/1994 |
| EP | 0638313 | 2/1995 |
| EP | 1304104 | 4/2003 |
| EP | 1413197 | 4/2004 |
| EP | 1707178 | 10/2006 |
| EP | 1932808 | 6/2008 |
| EP | 1946750 | 7/2008 |
| ES | 2018952 | 5/1991 |
| GB | 1336866 | 11/1973 |
| GB | 2031395 | 4/1980 |
| GB | 2254556 | 10/1992 |
| GB | 1378830 | 12/1994 |
| HU | 201880 | 1/1991 |
| IE | 63343 | 4/1995 |
| IN | 192168 | 3/2004 |
| JP | 61036222 | 2/1986 |
| JP | 62145024 | 6/1987 |
| JP | 05155776 | 6/1993 |
| JP | 05208816 | 8/1993 |
| JP | 10059842 | 3/1998 |
| JP | 10101569 | 4/1998 |
| JP | 10236960 | 9/1998 |
| JP | 3001114 | 1/2000 |
| JP | 2000086537 | 3/2000 |
| JP | 2001233619 A | 8/2001 |
| JP | 2001517633 | 10/2001 |
| JP | 2004089760 | 3/2004 |
| JP | 2007253030 A | 10/2007 |
| JP | 2008525292 A | 7/2008 |
| JP | 2009143798 A | 7/2009 |
| JP | 5105636 B2 | 12/2012 |
| PL | 189716 | 6/1997 |
| PL | 200957 | 11/1999 |
| SU | 414849 | 9/1977 |
| WO | WO-91/18835 | 12/1991 |
| WO | WO-92/01458 | 2/1992 |
| WO | WO-93/22237 | 11/1993 |
| WO | WO-94/09798 | 5/1994 |
| WO | WO-95/11033 | 4/1995 |
| WO | WO-95/29679 | 11/1995 |
| WO | WO-96/30029 | 10/1996 |
| WO | WO-97/11166 | 3/1997 |
| WO | WO-97/22266 | 6/1997 |
| WO | WO-97/26789 A1 | 7/1997 |
| WO | WO-97/48380 | 12/1997 |
| WO | WO-99/15189 | 4/1999 |
| WO | WO-99/44580 | 9/1999 |
| WO | WO-00/32189 | 6/2000 |
| WO | WO-01/27069 | 4/2001 |
| WO | WO-01/49301 | 7/2001 |
| WO | WO-03/013473 | 2/2003 |
| WO | WO-03/017980 | 3/2003 |
| WO | WO-03/028706 | 4/2003 |
| WO | WO-03/072084 | 9/2003 |
| WO | WO-03/092658 | 11/2003 |
| WO | WO-2004/016553 | 2/2004 |
| WO | WO-2004/018094 | 3/2004 |
| WO | WO-2005/009381 | 2/2005 |
| WO | WO-2005/012194 | 2/2005 |
| WO | WO-2005/018651 | 3/2005 |
| WO | WO-2005/027876 | 3/2005 |
| WO | WO-2006/066341 A1 | 6/2006 |
| WO | WO-2006/085079 | 8/2006 |
| WO | WO-2007/074909 | 7/2007 |
| WO | WO-2007/088343 | 8/2007 |
| WO | WO-2007/135362 | 11/2007 |
| WO | WO-2008/071747 | 6/2008 |
| WO | WO-2008/129034 | 10/2008 |
| WO | WO-2009/016349 | 2/2009 |
| WO | WO-2009/050468 | 4/2009 |

OTHER PUBLICATIONS

Ambrogi et al., Intercalation compounds of hydrotalcite-like anionic clays with anti-inflammatory agents, II: Uptake of diclofenac for a controlled release formulation, AAPS PharmSciTech., 3(3):E26 (2002).

Ansel et al., Pharmaceutical Dosage Forms and Drug Delivery Systems, Chapter 1-8 (pp. 1-243) Lippincott, Williams & Wilkins (1999).

Aoshima et al., Glycerin fatty acids esters as a new lubricant of tablets, Int. J. Pharm., 293:25-34 (2005).

Autissier et al., Relative in vitro efficacy of the phosphate binders lanthanum carbonate and sevelamer hydrochloride, J. Pharm. Sci., 96(10):2816-27 (2007).

Badawy et al., Effect of drug substance particle size on the characteristics of granulation manufactured in a high-shear mixer, AAPS PharmSciTech., 1(4):E33 (2000).

Badreddine et al.,Ion exchange of different phosphate ions into the zinc-aluminium-chloride layered double hydroxide, Materials Lett., 38(6): 391-5 (1999).

Barriga et al., Hydrotalcites as sorbent for 2,4,6-trinitrophenol: influence of the layer composition and interlayer anion, J. Mater. Chem., 12:1027-34 (2002).

(56) References Cited

OTHER PUBLICATIONS

Bejoy, Hydrotalcite: The Clay that Cures, Springer; Resonance, vol. 6 No. 2, pp. 57-61 (2001).
Bolhuis et al., Interaction of tablet disintegrants and magnesium strearate during mixing I: effect on tablet disintegration, J. Pharm. Sci., 70(12):1328-30 (1981).
Bolognini et al., Mg/Al mixed oxides prepared by coprecipitation and sol-gel routes: a comparison of their physico-chemical features and performances in m-cresol methylation, Microporous and Mesoporous Materials, 66:77-89 (2003).
Bothwell, Overview and mechanisms of iron regulation, Nutrition Rev., 53:237-45 (Sep. 1995).
Brouwers et al., Biopharmaceutical tests on antacids: in vitro and in vivo studies, Drugs Under Experiment. Clin. Res., 5:55-61 (1997).
Brouwers et al., De invloed van de toedieningsvorm op de weringsduur en op het pH-Bereik bij antacida: een in-vitro en in-vivo studie, Pharmaceutisch Weekblad, 111:1244-8 (1976) (abstract only).
Brouwers, Liquid Antacids, Pharmaceutisch Weekblad, 110:337-51 (1975) (abstract only).
Budavari et al. (eds.), The Merck Index, pp. 277, 331, and 917, Merck & Co. (1996).
Carlino, Chemistry between the sheets, Chemistry in Britain, pp. 59-62 (Sep. 1997).
Chatelet et al., Competition between monovalent and divalent anions for calcined and uncalcined hydrotalcite: anion exchange and adsorption sites, Colloids and Surfaces A: Physiochemical and Engineering Aspects, 111:167-75 (1996).
Chitrakar et al., Adsorption of phosphate from seawater on calcined MgMn-layered double hydroxides, J. Colloid Interface Sci., 290(1): 45-51 (2005).
Cook, Adaptation in iron metabolism, Am. J. Clin. Nutr., 51(2):301-8 (1990).
Das et al., Adsorption of phosphate by layered double hydroxides in aqueous solutions, Appl. Clay Sci., 32(3-4:252-60 (2006).
de Roy et al., Antionic Clays: Trends in Pillaring Chemistry, chapter 7, pp. 108-169 In: Synthesis of Microporous Mateirals (1992).
de Roy et al., Layered double hydroxides: synthesis and post-synthesis modification, Chapter I, pp. 33-34 In: Rives (ed.), Layered Double Hydroxides: Present and Future, Nova Science Publishers, Inc. (2001).
de Roy et al., Surface Text and Electron Microscopy Studies, pp. 243-244 In: Rives (ed.), Layered Double Hydroxides: Present and Future, Nova Science Publishers, Inc. (2001).
del Arco et al., Effect of the Mg:Al ratio on borate (or silicate)/nitrate exchange in hydrotalcite, J. Solid State Chem., 151(2):272-80 (2000).
del Arco et al., Surface and textural properties of hydrotalcite-like materials and their decomposition products, in: Rouquerol et al. (eds.), Characterization of Porous Solids III, Studies in Surface Science and Catalysis, vol. 87, pp. 507-515 (1994).
Drueke, Lanthanum carbonate as a first-line phosphate binder: the "cons", Semin. Dial., 20(4):329-32 (2007).
Emmett, A comparison of clinically useful phosphorus binders for patients with chronic kidney failure, Kidney Int.,66:S25-S32 (2004).
Erickson et al., A study of structural memory effects in synthetic hydrotalcites using environmental SEM, Materials Lett., 59:226-9 (2005).
Evans et al., "Structural Aspects of Layered Double Hydroxides" pp. 1-12, In: Duan et al. (eds.), Layered Double Hydroxides, vol. 119, Springer (2006).
Evonik Industries AG, product information for Eudragit® E100, Eudragit® E POA and Eudragit® E 12,5; pp. 1-6 (Oct. 2011).
Ferreira et al., Thermal decomposition and structural reconstruction effect on Mg Fe based hydrocalcite compounds, J. Solid State Chem., 177:3058-69 (2004).
Frost et al., Thermal decomposition of synthetic hydrotalcites reevesite and pyroaurite, J. Therm. Analysis Calorimetry, 76:217-25 (2004).
Grant et al. (eds.), Grant & Hackh's Chemical Dictionary, 5th edition, McGraw Hill, pp. 571 (1987).
Grubel et al., Interaction of an aluminum-magnesium containing antacid and gastric mucus: possible contribution to the cytoprotective function of antacids, Aliment. Pharmacol. Ther., 11(1):139-45 (1997).
Guillot et al., The use of magnesium-containing phosphate binders in patients with end-stage renal disease on maintenance hemodialysis, Nephron., 30(2):144-7 (1982).
Hansen et al., Formation of synthetic analogues of double metal-hydroxy carbonate minerals under controlled pH conditions: I. The synthesis of pyroaurite and reevesite, Clay Minerals, 25:161-79 (1990).
Hansen et al., Synthesis and characterization of pyroaurite, Appl. Clay Sci., 10(1-2):5-19 (1995).
Hansen et al., The use of glycerol intercalates in the exchange of $CO3^{2-}$ with $SO4^{2-}$, $NO3^-$ or $CL^-$ in pyroaurite-type compounds, Clay Minerals, 26:311-27 (1991).
Hashi et al., Preparation and properties of pyroaurite-like hydroxy minerals, Clays and Clay Minerals, 31(2):152-4 (1983).
He et al., Preparation of Layered Double Hydroxides, Struct. Bond., 119:89-119 (2006).
Hibino et al., Calcination and rehydration behavior of Mg—Fe—CO3 hydrotalcite-like compounds, J. Materials Sci. Lett., 19(16):1403-5 (2000).
Hirahara et al., Synthesis and antacid property of Mg—Fe layered double hydroxide, Nendo Kagaku—J. Clay Sci. Soc. of Japan, 42(2):70-6 (2002).
Hollander et al., Antacids vs. placebos in peptic ulcer therapy: a controlled double-blind investigation, JAMA, 226(10):1181-5 (1973).
Hudson et al., Thermal conversion of a layered (Mg/Al) double hydroxide to the oxide, J. Mater. Chem., 5(2):323-9 (1995).
International Preliminary Report on Patentability for corresponding international application No. PCT/GB2006/000452, issue date Aug. 14, 2007.
International Preliminary Report on Patentability for corresponding international application No. PCT/GB2010/051271, issuance date Feb. 7, 2012.
International Preliminary Report on Patentability for corresponding international application No. PCT/GB2011/050185, issuance date Aug. 7, 2012.
International Search Report and Written Opinion for corresponding international application No. PCT/GB2010/051271, mailing date Oct. 26, 2010.
International Search Report and Written Opinion for corresponding international application No. PCT/GB2011/050185, mailing date Feb. 6, 2012.
International Search Report for corresponding international application No. PCT/GB2006/000452, mailing date Oct. 12, 2006.
International Specialty Products, Pharmaceuticals Solid Dosage Forms (2004).
Iranloye et al., Effects of compression force, particle size and lubricants on dissolution rate, J. Pharm. Sci., 67(4):535-9 (1978).
Ishimura et al., "Hyper- and Hypophosphataemia" pp. 149-158, In: Morii et al. (eds.), Calcium in Internal Medicine, Springer (2002).
Kaplan et al., A preference study: calcium acetate tablets versus gelcaps in hemodialysis patients, Nephrol. Nurs. J., 29(4):363-5 (2002).
Kokot et al., A rotating disk study on the rates of hydrotalcite dissolution at 25° C, Pharmazie, 48 (H4):287-9 (1993).
Konorev et al., Selection of the optimal antacid drug in clinical practice, Consilium Medicum, vol. 5, issue 10 (2003).
Kostura et al., Rehydration of calcined Mg-Al hydrotalcite in acidified chloride-containing aqueous solution, Collect. Czech. Chem. Commun., 72:1284-94 (2007).
Kovanda et al., Thermal behavior of Ni-Mn layered double hydroxide and characterization of formed oxides, Solid State Sci., 5:1019-26 (2003).
Labajos et al., New layered double hydroxides with hydrotalcite structure containing Ni(II) and V(III), J. Materials Chem., 9:1033-9 (1999).

(56) References Cited

OTHER PUBLICATIONS

Larsson et al., Estimation of the bioavailability of iron and phosphorous in cereals using a dynamic in vitro gastrointestinal model, J. Sci. Food Agric., 74:99-106 (1997).
Lazaridis et al., Flotation of metal loaded clay anion exchangers, Part II: the case of arsenates, Chemosphere, 47:319-24 (2002).
Lazaridis et al., Flotation of metal loaded clay anion exchangers, Part II: the case of chromates, Chemosphere, 42:373-8 (2001).
Lazaridis, Sorption removal of anions and cations in single batch systems by uncalcined and calcined Mg—Al—CO3 hydrotalcite, Water Air Soil Pollution, 146:127-39 (2003).
Leinonen et al., Physical and lubrication properties of magnesium stearate, J. Pharm. Sci., 81(12):1194-8 (1992).
Li et al., Enteric-coated layered double hydroxides as a controlled release drug delivery system, Int. J. Pharm., 287(1-2):89-95 (2004).
Li et al., Stoichiometric Synthesis of Pure MFe2O4 (M = Mg, Co, and Ni) Spinel Ferrites from Tailored Layered Double Hydroxide (Hydrotalcite-Like) Precursors, Chem. Mater., 16(8):1597-602 (2004).
Lin et al., Evaluation of buffering capacity and acid neutralizing-pH time profile of antacids, J. Formos. Med. Assoc., 97:704-10 (1998).
Linares et al., The influence of hydrotalcite and cancrinite type zeolite in acidic aspirin solutions, Microporous and Mesoporous Materials, 74:105-10 (2004).
Llewellyn et al., The binding of bile acids by hydrocalcite and other antacid preparations, Pharmaceutica Acta Helvetiae, 52(1/2):1-5 (1977).
Logham-Adham, Safety of new phosphate binders for chronic renal failure, Drug Safety, 26(15):1093-1115 (2003).
MacCara, Acid neutralization capacity of Canadian antacid formulations, Can. Med. Assoc. J., 132:523-7 (1985).
Marchi et al., Impregnation-induced memory effect of thermally activated layered double hydroxide, Appl. Clay Sci., 13:35-48 (1998).
McCance et al., Absorption and excretion of iron, The Lancet, pp. 680-684 (Sep. 18, 1937).
McIntyre et al., Iron-magnesium hydroxycarbonate (Alpharen): a novel non calcium containing phosphate binder for the treatment of hyperphosphataemia in chronic haemodialysis patients, Nephrol. Dial. Transplant., 22 (suppl 6): vi171, FP452 Poster Session Abstract (Jun. 22, 2007).
Meng et al., Preparation and thermal decomposition of magnesium/iron (III) layered double hydroxide intercalated by hexacyanoferrate (III) ions, J. Mater. Sci., 39:4655-7 (2004).
Meng et al., Preparation of magnetic material containing MgFe2O4 spinel ferrite from a Mg—Fe(III) layered double hydroxide intercalated by hexacyanoferrate(III) ions, Mater.Chem. Phys., 86:1-4 (2004).
Merck Index, p. 969, entries 5694-707 (1996).
Mesh to Micron Conversion chart, retrieved from the Internet at <http:///www.shomegold.org/news/Mesh.htm>, accessed Sep. 27, 2012.
Miederer et al., Acid neutralization and bile acid binding capacity of hydrocalcite compared with other antacids: an in-vitro study, Chinese J. Digestive Diseases, 4(3):140-6 (2003).
Miyata et al., Physiochemical properties of synthetic hydrotalcites in relation to composition, Clays and Clay Minerals, 28(1):50-6 (1980).
Murthy et al., Effect of shear mixing on in vitro drug release of capsule formulations containing lubricants, J. Pharm. Sci., 66(9):1215-9 (1977).
Naylor et al., Use of gastrointestinal model and gastroplus for the prediction of in vivo performance, Industrial Pharmacy, 12:9-12 (2006).
Newman et al., Comparative study of some layered hydroxide salts containing exchangable interlayer anions, J. Solid State Chem., 148:26-40 (1999).
O'Donovan et al., Substitution of aluminium salts by magnesium salts in control of dialysis hyperphosphataemia, The Lancet, pp. 880-881 (Apr. 19, 1986).
Oe et al., Long-term use of magnesium hydroxide as a phosphate binder in patients on hemodialysis, Clin. Nephrol., 28(4):180-5 (1987).
Ookubo et al., Hydrotalcites as potential adsorbents of intestinal phosphate, J. Pharm. Sci., 81(11):1139-40 (1992).
Ookubo et al., Preparation and phosphate ion-exchange properties of a hydrotalcite-like compound, Langmuir, 9(5):1418-22 (1993).
Pesic et al., Thermal characteristics of a synthetic hydrotalcite like material, J. Mater. Chem., 2(10):1069-72 (1992).
Playle et al., The in-vitro antacid and anti-pepsin activity of hydrotalcite, Pharm. Acta Helv., 49(9/10:298-302 (1974).
Powell et al., The chemistry between aluminum in the gastrointestinal lumen and its uptake and absorption, Proc. Nutrition Soc., 52:241-53 (1993).
Rajamathi et al., Reversable thermal behaviour of the layered double hydroxide of Mg with Al: mechanistic studies, J. Mater. Chem., 10:2754-7 (2000).
Raki et al., Preparation, Characterization, and Moessbauer Spectroscopy of Organic Anion Intercalated Pyroaurite-like Layered Double Hydroxides, Chem. Mater., 7(1):221-4 (1995).
Rankin et al., The development and in-vitro evaluation of novel mixed metal hydroxy-carbonate compounds as phosphate binders, J. Pharm. Pharmacol., 53:361-9 (2001).
Reichle, Synthesis of anionic clay minerals (mixed metal hydroxides, hydrotalcite), Solid State Ionics, 22(1):135-41 (1986).
Remuzzi et al., Hematologic consequences of renal failure, The Kidney, vol. II, 5th ed. pp. 2170-2186 (1996).
Rives, Study of Layered Double Hydroxides by Thermal Methods, chapter 4, pp. 116-133 In: Rives (ed.), Layered Double Hydroxides: Present and Future, Nova Science Pub Inc. (2001).
Robolot et al., Effect of lubricant level and applied copressional pressure on surface friction of tablets, J. Pharm. Sci., 74(6):697-9 (1985).
Rodriguez-Benot et al., Mild hyperphosphatemia and mortality in hemodialysis patients, Am. J. Kidney Dis., 46(1):68-77 (2005).
Rubinstein et al., The effect of granule size on the in vitro and in vivo properties of bendrofluazide tablets 5mg, Pharm. Acta Helv., 52 (1/2): 5-10 (1977).
Rudnic et al., Oral Solid Dosage Forms, chapter 45, pp. 858-890 In: Gennaro (ed.), Remington: The Science and Practice of Pharmacy, 20th ed., Lippincott Williams & Wilkins (2000).
Sato et al., Adsorption of various anions by magnesium aluminum oxide Mg(0.7)Al(0.3)O(1.15), Ind. Eng. Chem. Prod. Res. Dev., 25:89-92 (1986).
Sato et al., Causticization of sodium carbonate with rock-salt-type magnesium aluminium oxide formed by the thermal decomposition of hydrotalcite-like layered double hydroxide, J. Chem. Tech. Biotechnol., 57:137-40 (1993).
Schwarz et al., Association of disorders in mineral metabolism with progression of chronic kidney disease, Clin. J. Am. Soc. Nephrol., 1:825-31 (2006).
Seida et al., Removal of phosphate by layered double hydroxides containing iron, Water Res., 36:1305-12 (2002).
Sheikh et al., Reducation of dietary phosphorus absorption by phosphorous binders: A theoretical, in vitro, and in vivo study, J. Clin. Invest., 83:66-73 (1989).
Shen et al., Preparation and characterization of Fe/MgO catalysts obtained from hydrotalcite-like compounds, Catalysis Today, 30(1-3):77-82 (1996).
Shin et al., Phosphorus removal by hydrotalcite-like compounds (HTLcs), Water Sci. Technol., 34(1-2):161-8 (1996).
Sigma-Aldrich product information for Iron(III) nitrate nonanhydrate, retrieved from the Internet: <http:www.sigmaaldrich.com> on Jun. 11, 2012 (one page).
Spengler et al., Cross-linked iron dextran is an efficient oral phosphate binder in the rat, Nephrol. Dial. Transplant., 11(5):808-12 (1996).
Stamatakis et al., Influence of pH on in vitro disintegration of phosphate binders, Am. J. Kidney Dis., 32(5):808-12 (1998).
Suren, Evaluation of lubricants in the development of tablet formulation, Dansk TIDSskr. Farm 45, pp. 331-338 (1971).

(56) References Cited

OTHER PUBLICATIONS

Tezuka et al, The Synthesis and Phosphate Adsorptive Properties of Mg(II)-Mn(III) Layered Double Hydroxides and Their Heat-Treated Materials, Bull Chem. Soc. Jpn. 2004, 77:2101-7 (2004).
The National Kidney Foundation Kidney Disease Quality Outcomes Initiative, Clinical Practice Guidelines for Bone Metabolism and Disease in Chronic Disease, Guide 5 pp. 1, pt. 5.5 (2003).
Tichit et al., Catalysis by hydrotalcites and related materials, Cattech, 7(6):206-17 (2003).
Titulaer et al., The formation of ice between hydrotalcite particles measured by thermoporometry, Clay Minerals, 31(2):263-77 (1996).
Trifiro et al, "Hydrotalcite-like Anionic Clays (Layered Double Hydroxides)", vol. 7, chapter 8, pp. 251-291, In: Alberti et al. (eds.) Comprehensive Supramolecular Chemistry, Pergamon, Oxford (1996).
Ulibarri et al., Kinetics of the thermal dehydration of some layered hydroxycarbonates, Thermochimica Acta, 135:231-6 (1998).
USANA Technical Bulletin, Tablet Excipients, Jun. 1999.
Van Der Voet et al., Intestinal absorption of aluminium from antacids: a comparison between hydrotalcite and algeldrate, Clin. Tech., 24(6):545-3 (1986).
Vatier et al., Antacid activity of calcium carbonate and hydrotalcite tablets, Arzneim-Forsch/Drug Res., 44(4):514-8 (1994).
Vitkova et al., The use of some hydrophobic substances in tablet technology, Milan Chilabala, Acta Pharamceutica Hungaria, 68:336-44 (1998).
Written Opinion for PCT/GB2007/000308, Nov. 30, 2007.
Zhang et al., Phosphorous anion exchange characteristic of a pyroaurite-like compound, Inorg. Mater., 4:132-8 (1997).
Zhang et al., Synthesis and characterization of a novel nanoscale magnetic solid base catalyst involving a layered double hydroxide supported on a ferrite core, J. Solid State Chem., 177:772-80 (2004).
Zhang et al., Synthesis of Mg/Fe pyroaurite-like compounds and their anion-exchange characteristics, Inorg. Mater., 2(259):480-5 (1995).
Zhao et al., Preparation of layered double-hydroxide nanomaterials with a uniform crystalite size using a new method involving separate nucleation and aging steps, Chem. Mater., 14(10):4286-91 (2002).
Zhu et al., Adsorption of phosphate by hydrotalcite and its calcined product, Acta Mineralogica Sinica, 25(1):27-32 (2005).
Zhu et al., Different Mg to Fe ratios in the mixed metal MgFe hydroxy-carbonate compounds and the effect on phosphate binding compared with established phosphate binders, J. Pharm. Sci., 91(1):53-66 (2002).
Dewberry et al., "Lanthanum carbonate: A novel non-calcium containing phosphate binder", *J Am Soc Nephrol*, 8:A2610 (1997).
Entry for "obtainable", Collins English Dictionary, retrieved from the Internet at <http://www.collinsdictionary.com> on May 15, 2013.
Fernandez et al., The effect of iron on the crystalline phases formed upon thermal decomposition of Mg—Al—Fe hydrotalcites, RCS Publishing: Journal of Materials Chemistry, 8(11):2507-14 (1998).
Forano, Environmental remediationinvolving layered double hydroxides, pp. 426-458, vol. 1, Elsevier Interface Science and Technology (2004).
Goh et al., Application of layered double hydroxides for removal of oxyanions: a review, Water Res., 42:1343-68 (2008).
Hansen et al., Reduction of nitrate to ammonium by sulphate green rust: activation energy and reaction mechanism, Clay Minerals, 33:87-101 (1998).
He et al., Hydrothermal Methods, p. 108 In: Duan et al. (eds.), Layered Double Hydroxides, Springer-Verlag Berlin Heidelberg (2006).
Merriam-Webster's Collegiate Dictionary—11th edition, entry for "prophylaxis" on p. 996 (2004).
Toth et al., Nano-scaled inorganic/biopolymer composites: molecular modeling vistas, AIChE Annual Meeting (2005).
Toth et al., Structure and energetics of biocompatible polymer nanocomposite systems: a molecular dynamics study, Biomacromolecules, 7:1714-9 (2006).
Tsuji et al., Hydrotalcites with an extended $Al^{3+}$-substitution: synthesis, simultaneous TG-DTA-MS study, and their $CO_2$ adsorption behaviors, J. Mater. Res., 8(5):1137-42 (1993).
Cargill et al., Chemical reactivity of aluminium-based pharmaceutical compounds used as phosphate-binders, J. Pharm. Pharmacol., 41:11-16 (1989).

\* cited by examiner

COMPOSITION COMPRISING MIXED METAL COMPOUNDS AND XANTHAN GUM

CROSS-REFERENCE TO RELATED APPLICATIONS

This is a U.S. National Stage of International Patent Application No. PCT/GB2011/050185 filed Feb. 3, 2011, which in turn claims the priority benefit of Great Britain Patent Application No. GB 1001779.6 filed Feb. 4, 2010, the entire respective disclosures of which are incorporated herein by reference.

The present invention relates to liquid formulation containing water-insoluble inorganic mixed metal compounds. The present invention further relates to methods of manufacture of the liquids and their use in unit and multiple dose forms for oral administration.

BACKGROUND OF THE INVENTION

Liquid Dosage Forms

Liquid dosage forms of insoluble compounds can provide a useful means of administration for subjects who have difficulty swallowing. In particular in the field of pharmaceuticals ease of administration may also help ensure optimal patient compliance. Additionally liquid form allows for a continuously variable dose quantity to be administered.

Many liquid doses forms of insoluble compounds are known from the art. For example, Altacite Plus Suspension (Peckforton Pharmaceuticals Limited) is sold as an antacid for the symptomatic relief of dyspepsia, flatulence and abdominal hyperacidity, gastritis, peptic ulceration, heartburn especially when associated with hiatus hernia, or heartburn during pregnancy. One of the active ingredients is 'hydrotalcite light', aluminium magnesium carbonate hydroxide hydrate. Altacite displays a yield stress of only 1 Pa and at this low yield stress would not be suitable for maintaining stable formulations wherein the active ingredient is of a hydrotalcite type comprising magnesium and iron or it is of insufficient yield stress to provide a stable formulation at a desirable particle size. and or dose level Another product from Peckforton Pharmaceuticals Limited, Hydrotalcite Suspension, also contains hydrotalcite. The formulation also contains Veegum regular which is a magnesium aluminum silicate used to alter the rheology of liquid formulation. However, as this is an aluminium source this product is not considered suitable for kidney patients.

Talcid is intended for the symptomatic relief in cases of heartburn, stomach hyperacidity. The active ingredient is 'hydrotalcite light', aluminium magnesium carbonate hydroxide hydrate, which suffers from the same drawback of aluminium release and accumulation. Furthermore, the formulation contains bentonite which at higher concentrations can modify the rheological characteristics of the formulation. Bentonite is a calcium hydrated aluminosilicate which may also release aluminium. Carboxymethylcellulose sodium is used as a thickening agent. Talcid displays some yield stress but insufficient to provide a stable formulation at a desirable particle size.

The delivery of mixed metal compound is particularly problematic because mixed metal compounds typically have a high particulate density (such as a density of around 1.9 g/ml). Due to the large difference in density between such compounds and that of typical aqueous carrier fluids, mixed metal compounds have a propensity to settle out on storage. The rheology of the carrier fluid may be modified to increase the viscosity of the fluid and hence slow the settling rate of the suspended solids. However because of the atypical high particulate density this has the disadvantage that whilst the settling rate is reduced settling will still occur over a relatively short time frame. Furthermore, the high fluid viscosity makes it difficult to re-disperse any settled mixed metal compound.

U.S. Pat. No. 4,689,219 describes compositions comprising mixtures of xanthan gum and locust bean gum in a specified range of ratios. The formulation is packaged as a dry granule mix which is added to a drink immediately prior to consumption.

WO2007/135362 describes a formulation based on xanthan gum, PVP and glycerol containing a suspended non-steroidal anti-inflammatory drug where PVP acts a dispersant and glycerol as a density increasing agent. The optimal PVP concentration disclosed is 0.5 to about 3.5% w/v. Further, the suspended non-steroidal anti-inflammatory drug is present at a concentration of up to 5% w/v. This compares to required delivery levels of typically 10% w/v for mixed metal compounds.

IE153343 discloses an aqueous suspension concentrate composition of pendimethalin, a pesticide. More specifically, IE153343 discloses the use of a suspending agent, such as xanthan gum, at a concentration between 0.02 and 3.0% w/v, in combination with thickening agents such as polyvinyl-pyrrolidone (PVP). The proposed compositions also include surfactants, dispensing agents or wetting agents and an antifoaming agent to provide a stable suspension.

U.S. Pat. No. 5,300,302 discloses a pharmaceutical delivery system comprising a composition comprising an drug homogeneously distributed in a water-dispersible gel excipient containing either xanthan gum or a mixture of xanthan gum and methyl cellulose.

WO 03/013473 A1 teaches a colloidal silicon dioxide which may be combined with xanthan gum and a wetting agent in order to produce a suspension of drug particles that is substantially stable. It is stated that silicon dioxide has a synergistic effect with xanthan gum and produces a more stable suspension than otherwise possible U.S. Pat. No. 5,112,604 discloses an aqueous formulation containing a drug substance; colloidal silicon dioxide; a hydrocolloid gum; a wetting agent; an antifoaming agent and a carbohydrate, which is stable for 90 days.

U.S. Pat. No. 7,300,670 discloses an aqueous pharmaceutical suspension for oral administration comprising at least one particulate drug with a density of from about 0.9 to about 1.6 g/ml and an average particle size less than about 20 micron; at least one suspending polymer exhibiting plastic flow with or without additional viscosity-building agents that provides a yield value to the final suspension of about 0.2 to about 15 Pa and an apparent viscosity at 100 $sec^{-1}$ of at least about 50 cps; a liquid phase with an absolute density difference from each particulate drug of less than about 0.2 g/ml.

To provide sterile compositions, the prior art has taught that liquid compositions may be irradiated. For example, U.S. Pat. No. 5,273,767 discloses a modified, rapidly hydrating xanthan gum, prepared by irradiating non-irradiated xanthan gum with ionizing radiation, and furthermore a process for sterilizing a food product comprising non-irradiated xanthan gum as a gelling hydrocolloid.

Although irradiation may provide sterility, it presents a number of problems when applied to liquids containing insoluble products. For example, "Formulation of a Sterile Surgical Lubricant", Adams, I., S. S. Davis and R, Kenshaw. 1972, J. Pharm. Pharmacol., 24:178P describes the complete loss of gel structure in methyl celluloses following irradiation. Applied Radiation Chemistry By Robert James Woods and Aleksei̇̆ Konstantinovich Pikaev teaches us that a standard irradiation doses of 25 kGy is used in many countries, and 35 kGy in Scandinavian countries, but that by control of the production environment microbial contamination can be reduced to levels down to 10 kGy. (Publisher Wiley-IEEE, 1994, ISBN 0471544523, 9780471544524). U.S. Pat. No. 7,259,192 describes the depolymerization by high energy electron beam irradiation of xanthan gum at a preferred dose of 10 to 150 kGy.

SUMMARY OF THE INVENTION

In a first aspect the present invention provides a composition comprising
(i) a mixed metal compound containing at least one trivalent metal selected from iron (III) and aluminium and at least one divalent metal selected from of magnesium, iron, zinc, calcium, lanthanum and cerium,
(ii) xanthan gum
(iii) at least one of
   (a) polyvinyl pyrrolidone
   (b) locust bean gum
   (c) methyl cellulose
wherein the composition has been irradiated with ionising radiation in an amount of at least 4 kGy.

In a second aspect the present invention provides a composition for use as a medicament, wherein the composition comprises
(i) a mixed metal compound containing at least one trivalent metal selected from iron (III) and aluminium and at least one divalent metal selected from of magnesium, iron, zinc, calcium, lanthanum and cerium,
(ii) xanthan gum
(iii) at least one of
   (a) polyvinyl pyrrolidone
   (b) locust bean gum
   (c) methyl cellulose
wherein the composition has been irradiated with ionising radiation in an amount of at least 4 kGy.

In a third aspect the present invention provides a composition for binding phosphate, wherein the composition comprises
(i) a mixed metal compound containing at least one trivalent metal selected from iron (III) and aluminium and at least one divalent metal selected from of magnesium, iron, zinc, calcium, lanthanum and cerium,
(ii) xanthan gum
(iii) at least one of
   (a) polyvinyl pyrrolidone
   (b) locust bean gum
   (c) methyl cellulose
wherein the composition has been irradiated with ionising radiation in an amount of at least 4 kGy.

In a fourth aspect the present invention provides a composition for use in the treatment of hyperphosphataemia, wherein the composition comprises
(i) a mixed metal compound containing at least one trivalent metal selected from iron (III) and aluminium and at least one divalent metal selected from of magnesium, iron, zinc, calcium, lanthanum and cerium,
(ii) xanthan gum
(iii) at least one of
   (a) polyvinyl pyrrolidone
   (b) locust bean gum
   (c) methyl cellulose
wherein the composition has been irradiated with ionising radiation in an amount of at least 4 kGy.

The present invention provides a carrier system for delivering insoluble mixed metal compounds, namely those containing at least one trivalent metal selected from iron (III) and aluminium and at least one divalent metal selected from of magnesium, iron, zinc, calcium, lanthanum and cerium. The present system avoids the disadvantages of the prior art systems either with regard to the problems associated with ingestion of the carrier or the detrimental effect that the carrier may have on the insoluble compound. Critically, many prior art carriers are significantly detrimental to the phosphate binding capacity of mixed metal compounds. Phosphate binding capacity is a key property of such compounds.

Many of the prior art excipients used to modify the rheology of the carrier fluid are anionic in nature and may therefore interact with the mixed metal compound, which binds phosphate by anion exchange. Consequently, the subsequent anion binding capacity of the mixed metal compound (in this case for phosphate) is hindered.

The present invention provides a system in which the use of oil-based carriers is avoided. Such carriers can have the drawback of a high relative calorific value. Such high calorific values are generally considered to be undesirable and are particularly unsuitable for subjects on a calorie restricted diet and/or who may consume the composition for a prolonged period of time.

The present invention is further advantageous in that it allows for high loads of mixed metal compound to be delivered. This is advantageous in that the volume of product required to deliver a determined amount of mixed metal compound is kept within acceptable amounts. The use of such high loads is particularly advantageous for subjects who desire or are required to control fluid intake. Such a group is patients on dialysis who must typically restrict the volume of liquid which they consume. Any aqueous liquid dose formulation will contribute to the volume of liquid which the patient consumes, hence the volume of liquid must be kept to a minimum. As the mixed metal compound may be used for binding phosphate in a subject or for treating hyperphosphataemia, the composition is to be administered to compounds suffering from renal disease who may in turn be undergoing dialysis. Thus the need to deliver high loads is particularly applicable when delivering mixed metal compounds.

The present invention is further advantageous in that it provides for a preserved liquid composition wherein the addition of preservative components is not required. Contrary to the teaching of the prior art, we have shown that by selection of a specific combination of suspension materials and selection of a specific radiation dosage, a stable and preserved composition may be provided. Prior art teachings in the field of effluent handling (Chromate immobilisation) showed that irradiation at 1000-6000 kGy is detrimental to mixed metal compounds and enhances the formation of spinell. In particular, we have shown that preservative components are not required. Mixed metal compounds in an un-buffered aqueous system at the concentration range of interest (ca. 10% w/v) provide a relatively high pH (ca. 9.2 to 9.4). The high pH excludes the use of all known, commercially available preservatives at concentrations effective for microbial control and at levels that are safe for use in a composition in a human population. For chemical preservation, the pH of the formulation must be limited to about 8.2 or below in order to permit the use of preservatives at concentrations that are safe in the human population. The preservative may have some efficacy above pH 8.2 however there is little margin for pH increase of the formulation, for example, on storage. A significant reduction in pH i.e. below approximately pH 8.0 cannot be made without releasing magnesium from the mixed metal compound structure. This has the effect of changing the mixed metal compound structure and may also impair properties such as phosphate binding performance of the mixed metal compound.

Hyperphosphataemia

As discussed herein in one aspect the present invention provides a composition for use in the treatment of hyperphosphataemia, wherein the composition comprises (i) a mixed metal compound containing at least one trivalent metal selected from iron (III) and aluminium and at least one divalent metal selected from of magnesium, iron, zinc, calcium, lanthanum and cerium, (ii) xanthan gum (iii) at least one of
  (a) polyvinyl pyrrolidone
  (b) locust bean gum
  (c) methyl cellulose wherein the composition has been irradiated with ionising radiation in an amount of at least 4 kGy.

Hyperphosphataemia is an electrolyte disturbance in which there is an abnormally elevated level of phosphate in blood. Hyperphosphataemia is frequently seen in dialysis patients, as standard dialysis regimes are unable to remove the ingested phosphate load even with a low phosphate diet, and is associated with an increased risk of death and the development of vascular calcification. The presence of hyperphosphataemia leads to hypocalcaemia, secondary hyperparathyroidism, reduced 1.25 Vit D3 and progressive metabolic bone disease. Elevated level of phosphate in blood is ultimately responsible for the increase in vascular calcification, but recent studies have also suggested that the process may additionally be influenced by 1.25 Vit D3 and an elevated calcium-phosphate product. Patients who have chronically uncontrolled hyperphosphataemia develop progressively extensive soft tissue calcifications due to the deposit of Calcium/phosphate product into skin, joints, tendons, ligaments. Eye deposits of calcium/phosphate product have also been described.

Control of serum phosphate levels using oral phosphate binders has, therefore, become a key therapeutic target in the management of dialysis patients. These binders, taken with food, render the contained phosphate insoluble and, therefore, non-absorbable.

For ease of reference, these and further aspects of the present invention are now discussed under appropriate section headings. However, the teachings under each section are not necessarily limited to each particular section.

Preferred Aspects

Component (i)—Mixed Metal Compound

The mixed metal compound utilised in the present invention may be any mixed metal compound containing at least one trivalent metal selected from iron (III) and aluminium and at least one divalent metal selected from of magnesium, iron, zinc, calcium, lanthanum and cerium. In one preferred aspect, the mixed metal compound contains at least iron (III) and at least magnesium.

Preferably, the compound is of formula I

$$M^{II}_{1-x}M^{III}_{x}(OH)_2A^{n-}_{y/n}.mH_2O \qquad (I)$$

wherein $M^{II}$ is one or more bivalent metals and is at least $Mg^{2+}$;
$M^{III}$ is one or more trivalent metals and is at least $Fe^{3+}$;
$A^{n-}$ is one or more n-valent anions and is at least $CO_3^{2-}$;
$(\Sigma yn)/x$ is from 0.5 to 1.5
$0 < x \le 0.4$,
$0 < y \le 1$ and
$0 < m \le 10$.

$(\Sigma yn)/x$ may preferably be from 0.6 to 1.4, such as 0.7 to 1.3, such as 0.8 to 1.2, such as 0.9 to 1.1, such as approximately 1, such as 1.0.

In one preferred aspect the compound has an aluminium content of less than 10,000 ppm, more preferably less than 7,000 ppm, more preferably less than 5,000 ppm, more preferably less than 3,000 ppm, more preferably less than 1000 ppm, more preferably less than 700 ppm, more preferably less than 500 ppm, more preferably less than 300 ppm, more preferably less than 200 ppm, most preferred 100 ppm, more preferably less than 50 ppm, most preferably 30 ppm.

In one aspect the mixed metal compound is a compound as described in WO99/015189.

In one aspect the mixed metal compound is a compound as described in WO2006/085079

In one aspect the mixed metal compound is a compound as described in WO 2009/050468.

In one aspect the mixed metal compound is a compound prepared in accordance with British Patent Application No. 0913525.2.

Preferably the compound has a d50 average particle size of less than 300 μm. Preferably the compound has a d50 average particle size of less than 200 μm. Preferably the compound has a d50 average particle size of less than 100 μm. Preferably the compound has a d50 average particle size of from 2 to 50 μm. Preferably the compound has a d50 average particle size of from 2 to 30 μm.

The present invention encompasses products obtained by virtue of further treatment. In one aspect the dried crude product is milled. More preferably the dried crude product is milled to a d50 average particle size of less than 10 μm, yet more preferably the dried crude product is milled to a d50 average particle size from 2-10 μm. most preferred the dried crude product is milled to a d50 average particle size from 2-7 μm, yet most preferred the dried crude product is milled to a d50 average particle size of approximately 5 μm.

The physical stability of the present composition may be further improved by reducing the particle size of the mixed metal compound by e.g. micronisation or wet milling.

The physical stability of the present composition may also be further improved by drying the mixed metal compound prior to incorporation in the composition. We found, surprisingly, that drying the mixed metal compound to a moisture content of <15% w/w produces a mixed metal compound which is stable in the present aqueous liquid formulation. By contrast, un-dried mixed metal compound (i.e. mixed metal compound synthesised by reaction in the normal way but washed and filtered without drying) is less stable when made up into a liquid.

In one preferred aspect the mixed metal compound is present in an amount of 8 to 12 w/v, more preferably the mixed metal compound is present in an amount of approximately 10 w/v.

The mixed metal compound may have a particle density (as measured in accordance with method 20) of greater than 1.6 g/ml, or greater than 1.9 g/ml. Moreover, the difference between the particle density of the mixed metal compound and the fluid of the composition (typically comprised of component (ii) and component (iii)) is greater than 0.2 g/ml.

Irradiation

As discussed herein the present composition is irradiated with ionising radiation in an amount of at least 4 kGy. Preferably the composition has been irradiated with ionising radiation in an amount of at least 6 kGy, such as in an amount of at least 8 kGy, such as in an amount of at least 10 kGy. Preferably the composition has been irradiated with ionising radiation in an amount of no greater than 20 kGy, such as in an amount of no greater than 15 kGy, such as in an amount of no greater than 12 kGy, such as in an amount of no greater than 10 kGy. The present composition may be irradiated with ionising radiation in an amount of 1 to 15 kGy, such as 2 to 14 kGy, such as 4 to 12 kGy, such as 6 to 10 kGy. Preferably the composition has been irradiated with ionising radiation in an amount of from 4 to 20 kGy, such as in an amount of from 4 to 15 kGy, such as in an amount of from 4 to 12 kGy, such as in an amount of from 4 to 10 kGy. Preferably the composition has been irradiated with ionising radiation in an amount of from 6 to 20 kGy, such as in an amount of from 6 to 15 kGy, such as in an amount of from 6 to 12 kGy, such as in an amount of from 6 to 10 kGy.

Any suitable source of ionising irradiation may be used to provide the desired level of irradiation. It is envisaged that electron beam, gamma and x-ray irradiation will be preferred.

Component (ii)—Xanthan Gum

Xanthan gum is a natural anionic biopolysaccharide made up of different monosacharides, mannose, glucose and glucuronic acids. It has the advantage over other common natural polymers of resisting degradation by enzymes. Suspensions using xanthan gums have the advantage that once the yield stress is exceeded, they are shearing thinning i.e. the viscosity reduces with increasing shear input. Therefore, if settling occurs, shear input can be applied (by, for example shaking of the liquid container) to reduce the viscosity and thus aid re-dispersion of any settled solids. As discussed herein, the present composition must contain xanthan gum. One skilled in the art will appreciate that the xanthan gum may be present in any suitable amount sufficient to achieve the aims of the invention.

In one aspect the xanthan gum is present in an amount of no greater than 10 wt %, preferably in an amount of no greater than 7 wt %, preferably in an amount of no greater than 5 wt %, preferably in an amount of no greater than 3 wt %, preferably in an amount of no greater than 2 wt %, preferably in an amount of no greater than 1.5 wt %, preferably in an amount of no greater than 1 wt %, preferably in an amount of no greater than 0.8 wt %, preferably in an amount of no greater than 0.6 wt %, preferably in an amount of no greater than 0.5 wt % based on weight of the composition.

In one aspect the xanthan gum is present in an amount of no less than 0.01 wt %, preferably in an amount of no less than 0.02 wt %, preferably in an amount of no less than 0.03 wt %, preferably in an amount of no less than 0.05 wt %, preferably in an amount of no less than 0.08 wt %, preferably in an amount of no less than 0.1 wt %, preferably in an amount of no less than 0.2 wt %, preferably in an amount of no less than 0.3 wt % based on weight of the composition.

In one aspect the xanthan gum is present in an amount of from 0.01 to 10 wt %, preferably in an amount of from 0.02 to 7 wt %, preferably in an amount of from 0.03 to 5 wt %, preferably in an amount of from 0.05 to 3 wt %, preferably in an amount of from 0.08 to 2 wt %, preferably in an amount of from 0.1 to 1 wt %, preferably in an amount of from 0.2 to 0.8 wt %, preferably in an amount of from 0.2 to 0.6 wt %, preferably in an amount of from 0.2 to 0.5 wt %, preferably in an amount of from 0.3 to 0.5 wt % based on weight of the composition.

Component (iii)

As discussed herein, the present composition must contain at least one of (a) polyvinyl pyrrolidone, (b) locust bean gum, and (c) methyl cellulose. It will be appreciated by one skilled in the art that by at least of it is meant that one of the listed components may be present, two of the listed components may be present or all three of the listed components may be present. The one, two or three listed components may be present in any suitable amount sufficient to achieve the aims of the invention.

In one aspect the present composition contains polyvinyl pyrrolidone. In one aspect the present composition contains locust bean gum. In one aspect the present composition contains methyl cellulose. In one aspect the present composition contains polyvinyl pyrrolidone and locust bean gum. In one aspect the present composition contains polyvinyl pyrrolidone and methyl cellulose. In one aspect the present composition contains locust bean gum and methyl cellulose. In one aspect the present composition contains polyvinyl pyrrolidone, locust bean gum, and methyl cellulose.

Locust bean gum is a high molecular weight, hydrophilic polysaccharide. It is non-ionic and is therefore unlikely to compete with phosphate by binding to the mixed metal compound.

In one aspect component (iii) is present in an amount of no greater than 10 wt %, preferably in an amount of no greater than 7 wt %, preferably in an amount of no greater than 5 wt %, preferably in an amount of no greater than 3 wt %, preferably in an amount of no greater than 2 wt %, preferably in an amount of no greater than 1.5 wt %, preferably in an amount of no greater than 1 wt %, preferably in an amount of no greater than 0.8 wt %, preferably in an amount of no greater than 0.6 wt %, preferably in an amount of no greater than 0.5 wt % based on weight of the composition. It will be understood that each of the above amounts refers to the combined total amount of (a) polyvinyl pyrrolidone, (b) locust bean gum, and (c) methyl cellulose.

In one polyvinyl pyrrolidone is present in an amount of no greater than 10 wt %, preferably in an amount of no greater than 7 wt %, preferably in an amount of no greater than 5 wt %, preferably in an amount of no greater than 3 wt %, preferably in an amount of no greater than 2 wt %, preferably in an amount of no greater than 1.5 wt %, preferably in an amount of no greater than 1 wt %, preferably in an amount of no greater than 0.8 wt %, preferably in an amount of no greater than 0.6 wt %, preferably in an amount of no greater than 0.5 wt % based on weight of the composition.

In one aspect locust bean gum is present in an amount of no greater than 10 wt %, preferably in an amount of no greater than 7 wt %, preferably in an amount of no greater than 5 wt %, preferably in an amount of no greater than 3 wt %, preferably in an amount of no greater than 2 wt %, preferably in an amount of no greater than 1.5 wt %, preferably in an amount of no greater than 1 wt %, preferably in an amount of no greater than 0.8 wt %, preferably in an amount of no greater than 0.6 wt %, preferably in an amount of no greater than 0.5 wt % based on weight of the composition.

In one aspect methyl cellulose is present in an amount of no greater than 10 wt %, preferably in an amount of no greater than 7 wt %, preferably in an amount of no greater than 5 wt %, preferably in an amount of no greater than 3 wt %, preferably in an amount of no greater than 2 wt %, preferably in an amount of no greater than 1.5 wt %, preferably in an amount of no greater than 1 wt %, preferably in an amount of no greater than 0.8 wt %, preferably in an amount of no greater than 0.6 wt %, preferably in an amount of no greater than 0.5 wt % based on weight of the composition.

In one aspect component (iii) is present in an amount of no less than 0.01 wt %, preferably in an amount of no less than 0.02 wt %, preferably in an amount of no less than 0.03 wt %, preferably in an amount of no less than 0.05 wt %, preferably in an amount of no less than 0.08 wt %, preferably in an amount of no less than 0.1 wt %, preferably in an amount of no less than 0.2 wt %, preferably in an amount of no less than 0.3 wt % based on weight of the composition. It will be understood that each of the above amounts refers to the combined total amount of (a) polyvinyl pyrrolidone, (b) locust bean gum, and (c) methyl cellulose.

In one aspect polyvinyl pyrrolidone is present in an amount of no less than 0.01 wt %, preferably in an amount of no less than 0.02 wt %, preferably in an amount of no less than 0.03 wt %, preferably in an amount of no less than 0.05 wt %, preferably in an amount of no less than 0.08 wt %, preferably in an amount of no less than 0.1 wt %, preferably in an amount of no less than 0.2 wt %, preferably in an amount of no less than 0.3 wt % based on weight of the composition.

In one locust bean gum is present in an amount of no less than 0.0 wt %, preferably in an amount of no less than 0.02 wt %, preferably in an amount of no less than 0.03 wt %, preferably in an amount of no less than 0.05 wt %, preferably in an amount of no less than 0.08 wt %, preferably in an amount of no less than 0.1 wt %, preferably in an amount of no less than 0.2 wt %, preferably in an amount of no less than 0.3 wt % based on weight of the composition.

In one aspect methyl cellulose is present in an amount of no less than 0.01 wt %, preferably in an amount of no less than 0.02 wt %, preferably in an amount of no less than 0.03 wt %, preferably in an amount of no less than 0.05 wt %, preferably in an amount of no less than 0.08 wt %, preferably in an amount of no less than 0.1 wt %, preferably in an amount of no less than 0.2 wt %, preferably in an amount of no less than 0.3 wt % based on weight of the composition.

In one aspect component (iii) is present in an amount of from 0.01 to 10 wt %, preferably in an amount of from 0.02 to 7 wt %, preferably in an amount of from 0.03 to 5 wt %, preferably in an amount of from 0.05 to 3 wt %, preferably in an amount of from 0.08 to 2 wt %, preferably in an amount of from 0.1 to 1 wt %, preferably in an amount of from 0.2 to 0.8 wt %, preferably in an amount of from 0.2 to 0.6 wt %, preferably in an amount of from 0.2 to 0.5 wt %, preferably in an amount of from 0.3 to 0.5 wt % based on weight of the composition. It will be understood that each of the above amounts refers to the combined total amount of (a) polyvinyl pyrrolidone, (b) locust bean gum, and (c) methyl cellulose.

In one aspect polyvinyl pyrrolidone is present in an amount of from 0.01 to 10 wt %, preferably in an amount of from 0.02 to 7 wt %, preferably in an amount of from 0.03 to 5 wt %, preferably in an amount of from 0.05 to 3 wt %, preferably in an amount of from 0.08 to 2 wt %, preferably in an amount of from 0.1 to 1 wt %, preferably in an amount of from 0.2 to 0.8 wt %, preferably in an amount of from 0.2 to 0.6 wt %, preferably in an amount of from 0.2 to 0.5 wt %, preferably in an amount of from 0.3 to 0.5 wt % based on weight of the composition.

In one aspect locust bean gum is present in an amount of from 0.01 to 10 wt %, preferably in an amount of from 0.02 to 7 wt %, preferably in an amount of from 0.03 to 5 wt %, preferably in an amount of from 0.05 to 3 wt %, preferably in an amount of from 0.08 to 2 wt %, preferably in an amount of from 0.1 to 1 wt %, preferably in an amount of from 0.2 to 0.8 wt %, preferably in an amount of from 0.2 to 0.6 wt %, preferably in an amount of from 0.2 to 0.5 wt %, preferably in an amount of from 0.3 to 0.5 wt % based on weight of the composition.

In one aspect methyl cellulose is present in an amount of from 0.01 to 10 wt %, preferably in an amount of from 0.02 to 7 wt %, preferably in an amount of from 0.03 to 5 wt %, preferably in an amount of from 0.05 to 3 wt %, preferably in an amount of from 0.08 to 2 wt %, preferably in an amount of from 0.1 to 1 wt %, preferably in an amount of from 0.2 to 0.8 wt %, preferably in an amount of from 0.2 to 0.6 wt %, preferably in an amount of from 0.2 to 0.5 wt %, preferably in an amount of from 0.3 to 0.5 wt % based on weight of the composition.

Component (iv) Sweeteners

Optionally, the palatability of the formulation may be improved by the addition of sweeteners (either alone or in combination with sorbitol) and/or flavourings. For example, sweeteners such as Acesulfame K/Aspartame, Xylitol, Thaumatin (Talin) and Saccharin; and flavourings such as Butterscotch, Caramel, Vanilla, Mild peppermint and Strawberry, may be used.

Composition

The preferred absolute amounts of xanthan gum and component (iii), namely at least one of (a) polyvinyl pyrrolidone (b) locust bean gum and (c) methyl cellulose are defined herein. The ratio of xanthan gum and component (iii) may be any suitable ratio within the absolute amounts described herein. In one aspect the xanthan gum and component (iii) are present in a ratio of 2:1 to 1:2. Preferably the xanthan gum and component (iii) are present in a ratio of approximately 1:1.

When the composition comprises at least polyvinyl pyrrolidone, preferably the composition comprises (ii) xanthan gum and (iii) polyvinyl pyrrolidone, wherein the xanthan gum and polyvinyl pyrrolidone are present in a ratio of approximately 2:1. In this aspect preferably the composition has been irradiated with ionising radiation in an amount of at least 8 kGy.

When the composition comprises at least locust bean gum, preferably the composition comprises (ii) xanthan gum and (iii) locust bean gum, wherein the xanthan gum and locust bean gum are present in a ratio of approximately 1:1. In this aspect preferably the composition has been irradiated with ionising radiation in an amount of at least 6 kGy.

When the composition comprises at least methyl cellulose, preferably the composition comprises (ii) xanthan gum and (iii) methyl cellulose, wherein the xanthan gum and methyl cellulose are present in a ratio of approximately 1:1. In this aspect preferably the composition has been irradiated with ionising radiation in an amount of at least 10 kGy.

The following compositions are preferred

Polyvinyl Pyrrolidone Containing Compositions

| xanthan gum | polyvinyl pyrrolidone |
|---|---|
| based on weight of the composition | |
| from 0.01 to 10 wt % | from 0.01 to 10 wt %; or |
| | from 0.02 to 7 wt %; or |
| | from 0.03 to 5 wt %; or |

-continued

| xanthan gum | polyvinyl pyrrolidone |
|---|---|
| | based on weight of the composition |
| | from 0.05 to 3 wt %; or |
| | from 0.08 to 2 wt %; or |
| | from 0.1 to 1 wt %; or |
| | from 0.2 to 0.8 wt %; or |
| | from 0.2 to 0.6 wt %; or |
| | from 0.2 to 0.5 wt %; or |
| | from 0.3 to 0.5 wt %. |
| from 0.02 to 7 wt % | from 0.01 to 10 wt %; or |
| | from 0.02 to 7 wt %; or |
| | from 0.03 to 5 wt %; or |
| | from 0.05 to 3 wt %; or |
| | from 0.08 to 2 wt %; or |
| | from 0.1 to 1 wt %; or |
| | from 0.2 to 0.8 wt %; or |
| | from 0.2 to 0.6 wt %; or |
| | from 0.2 to 0.5 wt %; or |
| | from 0.3 to 0.5 wt %. |
| from 0.03 to 5 wt % | from 0.01 to 10 wt %; or |
| | from 0.02 to 7 wt %; or |
| | from 0.03 to 5 wt %; or |
| | from 0.05 to 3 wt %; or |
| | from 0.08 to 2 wt %; or |
| | from 0.1 to 1 wt %; or |
| | from 0.2 to 0.8 wt %; or |
| | from 0.2 to 0.6 wt %; or |
| | from 0.2 to 0.5 wt %; or |
| | from 0.3 to 0.5 wt %. |
| from 0.05 to 3 wt % | from 0.01 to 10 wt %; or |
| | from 0.02 to 7 wt %; or |
| | from 0.03 to 5 wt %; or |
| | from 0.05 to 3 wt %; or |
| | from 0.08 to 2 wt %; or |
| | from 0.1 to 1 wt %; or |
| | from 0.2 to 0.8 wt %; or |
| | from 0.2 to 0.6 wt %; or |
| | from 0.2 to 0.5 wt %; or |
| | from 0.3 to 0.5 wt %. |
| from 0.08 to 2 wt % | from 0.01 to 10 wt %; or |
| | from 0.02 to 7 wt %; or |
| | from 0.03 to 5 wt %; or |
| | from 0.05 to 3 wt %; or |
| | from 0.08 to 2 wt %; or |
| | from 0.1 to 1 wt %; or |
| | from 0.2 to 0.8 wt %; or |
| | from 0.2 to 0.6 wt %; or |
| | from 0.2 to 0.5 wt %; or |
| | from 0.3 to 0.5 wt %. |
| from 0.1 to 1 wt % | from 0.01 to 10 wt %; or |
| | from 0.02 to 7 wt %; or |
| | from 0.03 to 5 wt %; or |
| | from 0.05 to 3 wt %; or |
| | from 0.08 to 2 wt %; or |
| | from 0.1 to 1 wt %; or |
| | from 0.2 to 0.8 wt %; or |
| | from 0.2 to 0.6 wt %; or |
| | from 0.2 to 0.5 wt %; or |
| | from 0.3 to 0.5 wt %. |
| from 0.2 to 0.8 wt % | from 0.01 to 10 wt %; or |
| | from 0.02 to 7 wt %; or |
| | from 0.03 to 5 wt %; or |
| | from 0.05 to 3 wt %; or |
| | from 0.08 to 2 wt %; or |
| | from 0.1 to 1 wt %; or |
| | from 0.2 to 0.8 wt %; or |
| | from 0.2 to 0.6 wt %; or |
| | from 0.2 to 0.5 wt %; or |
| | from 0.3 to 0.5 wt %. |
| from 0.2 to 0.6 wt % | from 0.01 to 10 wt %; or |
| | from 0.02 to 7 wt %; or |
| | from 0.03 to 5 wt %; or |
| | from 0.05 to 3 wt %; or |
| | from 0.08 to 2 wt %; or |
| | from 0.1 to 1 wt %; or |
| | from 0.2 to 0.8 wt %; or |
| | from 0.2 to 0.6 wt %; or |
| | from 0.2 to 0.5 wt %; or |

-continued

| xanthan gum | polyvinyl pyrrolidone |
|---|---|
| | based on weight of the composition |
| | from 0.3 to 0.5 wt %. |
| from 0.2 to 0.5 wt % | from 0.01 to 10 wt %; or |
| | from 0.02 to 7 wt %; or |
| | from 0.03 to 5 wt %; or |
| | from 0.05 to 3 wt %; or |
| | from 0.08 to 2 wt %; or |
| | from 0.1 to 1 wt %; or |
| | from 0.2 to 0.8 wt %; or |
| | from 0.2 to 0.6 wt %; or |
| | from 0.2 to 0.5 wt %; or |
| | from 0.3 to 0.5 wt %. |
| from 0.3 to 0.5 wt %. | from 0.01 to 10 wt %; or |
| | from 0.02 to 7 wt %; or |
| | from 0.03 to 5 wt %; or |
| | from 0.05 to 3 wt %; or |
| | from 0.08 to 2 wt %; or |
| | from 0.1 to 1 wt %; or |
| | from 0.2 to 0.8 wt %; or |
| | from 0.2 to 0.6 wt %; or |
| | from 0.2 to 0.5 wt %; or |
| | from 0.3 to 0.5 wt %. |

Locust Bean Gum Containing Compositions

| xanthan gum | locust bean gum |
|---|---|
| | based on weight of the composition |
| from 0.01 to 10 wt % | from 0.01 to 10 wt %; or |
| | from 0.02 to 7 wt %; or |
| | from 0.03 to 5 wt %; or |
| | from 0.05 to 3 wt %; or |
| | from 0.08 to 2 wt %; or |
| | from 0.1 to 1 wt %; or |
| | from 0.2 to 0.8 wt %; or |
| | from 0.2 to 0.6 wt %; or |
| | from 0.2 to 0.5 wt %; or |
| | from 0.3 to 0.5 wt %. |
| from 0.02 to 7 wt % | from 0.01 to 10 wt %; or |
| | from 0.02 to 7 wt %; or |
| | from 0.03 to 5 wt %; or |
| | from 0.05 to 3 wt %; or |
| | from 0.08 to 2 wt %; or |
| | from 0.1 to 1 wt %; or |
| | from 0.2 to 0.8 wt %; or |
| | from 0.2 to 0.6 wt %; or |
| | from 0.2 to 0.5 wt %; or |
| | from 0.3 to 0.5 wt %. |
| from 0.03 to 5 wt % | from 0.01 to 10 wt %; or |
| | from 0.02 to 7 wt %; or |
| | from 0.03 to 5 wt %; or |
| | from 0.05 to 3 wt %; or |
| | from 0.08 to 2 wt %; or |
| | from 0.1 to 1 wt %; or |
| | from 0.2 to 0.8 wt %; or |
| | from 0.2 to 0.6 wt %; or |
| | from 0.2 to 0.5 wt %; or |
| | from 0.3 to 0.5 wt %. |
| from 0.05 to 3 wt % | from 0.01 to 10 wt %; or |
| | from 0.02 to 7 wt %; or |
| | from 0.03 to 5 wt %; or |
| | from 0.05 to 3 wt %; or |
| | from 0.08 to 2 wt %; or |
| | from 0.1 to 1 wt %; or |
| | from 0.2 to 0.8 wt %; or |
| | from 0.2 to 0.6 wt %; or |
| | from 0.2 to 0.5 wt %; or |
| | from 0.3 to 0.5 wt %. |
| from 0.08 to 2 wt % | from 0.01 to 10 wt %; or |
| | from 0.02 to 7 wt %; or |
| | from 0.03 to 5 wt %; or |
| | from 0.05 to 3 wt %; or |
| | from 0.08 to 2 wt %; or |
| | from 0.1 to 1 wt %; or |
| | from 0.2 to 0.8 wt %; or |

| xanthan gum | locust bean gum |
|---|---|
| | based on weight of the composition |
| | from 0.2 to 0.6 wt %; or |
| | from 0.2 to 0.5 wt %; or |
| | from 0.3 to 0.5 wt %. |
| from 0.1 to 1 wt % | from 0.01 to 10 wt %; or |
| | from 0.02 to 7 wt %; or |
| | from 0.03 to 5 wt %; or |
| | from 0.05 to 3 wt %; or |
| | from 0.08 to 2 wt %; or |
| | from 0.1 to 1 wt %; or |
| | from 0.2 to 0.8 wt %; or |
| | from 0.2 to 0.6 wt %; or |
| | from 0.2 to 0.5 wt %; or |
| | from 0.3 to 0.5 wt %. |
| from 0.2 to 0.8 wt % | from 0.01 to 10 wt %; or |
| | from 0.02 to 7 wt %; or |
| | from 0.03 to 5 wt %; or |
| | from 0.05 to 3 wt %; or |
| | from 0.08 to 2 wt %; or |
| | from 0.1 to 1 wt %; or |
| | from 0.2 to 0.8 wt %; or |
| | from 0.2 to 0.6 wt %; or |
| | from 0.2 to 0.5 wt %; or |
| | from 0.3 to 0.5 wt %. |
| from 0.2 to 0.6 wt % | from 0.01 to 10 wt %; or |
| | from 0.02 to 7 wt %; or |
| | from 0.03 to 5 wt %; or |
| | from 0.05 to 3 wt %; or |
| | from 0.08 to 2 wt %; or |
| | from 0.1 to 1 wt %; or |
| | from 0.2 to 0.8 wt %; or |
| | from 0.2 to 0.6 wt %; or |
| | from 0.2 to 0.5 wt %; or |
| | from 0.3 to 0.5 wt %. |
| from 0.2 to 0.5 wt % | from 0.01 to 10 wt %; or |
| | from 0.02 to 7 wt %; or |
| | from 0.03 to 5 wt %; or |
| | from 0.05 to 3 wt %; or |
| | from 0.08 to 2 wt %; or |
| | from 0.1 to 1 wt %; or |
| | from 0.2 to 0.8 wt %; or |
| | from 0.2 to 0.6 wt %; or |
| | from 0.2 to 0.5 wt %; or |
| | from 0.3 to 0.5 wt %. |
| from 0.3 to 0.5 wt %. | from 0.01 to 10 wt %; or |
| | from 0.02 to 7 wt %; or |
| | from 0.03 to 5 wt %; or |
| | from 0.05 to 3 wt %; or |
| | from 0.08 to 2 wt %; or |
| | from 0.1 to 1 wt %; or |
| | from 0.2 to 0.8 wt %; or |
| | from 0.2 to 0.6 wt %; or |
| | from 0.2 to 0.5 wt %; or |
| | from 0.3 to 0.5 wt %. |

Methyl Cellulose Containing Compositions

| xanthan gum | methyl cellulose |
|---|---|
| | based on weight of the composition |
| from 0.01 to 10 wt % | from 0.01 to 10 wt %; or |
| | from 0.02 to 7 wt %; or |
| | from 0.03 to 5 wt %; or |
| | from 0.05 to 3 wt %; or |
| | from 0.08 to 2 wt %; or |
| | from 0.1 to 1 wt %; or |
| | from 0.2 to 0.8 wt %; or |
| | from 0.2 to 0.6 wt %; or |
| | from 0.2 to 0.5 wt %; or |
| | from 0.3 to 0.5 wt %. |
| from 0.02 to 7 wt % | from 0.01 to 10 wt %; or |
| | from 0.02 to 7 wt %; or |
| | from 0.03 to 5 wt %; or |
| | from 0.05 to 3 wt %; or |
| | from 0.08 to 2 wt %; or |
| | from 0.1 to 1 wt %; or |
| | from 0.2 to 0.8 wt %; or |
| | from 0.2 to 0.6 wt %; or |
| | from 0.2 to 0.5 wt %; or |
| | from 0.3 to 0.5 wt %. |
| from 0.03 to 5 wt % | from 0.01 to 10 wt %; or |
| | from 0.02 to 7 wt %; or |
| | from 0.03 to 5 wt %; or |
| | from 0.05 to 3 wt %; or |
| | from 0.08 to 2 wt %; or |
| | from 0.1 to 1 wt %; or |
| | from 0.2 to 0.8 wt %; or |
| | from 0.2 to 0.6 wt %; or |
| | from 0.2 to 0.5 wt %; or |
| | from 0.3 to 0.5 wt %. |
| from 0.05 to 3 wt % | from 0.01 to 10 wt %; or |
| | from 0.02 to 7 wt %; or |
| | from 0.03 to 5 wt %; or |
| | from 0.05 to 3 wt %; or |
| | from 0.08 to 2 wt %; or |
| | from 0.1 to 1 wt %; or |
| | from 0.2 to 0.8 wt %; or |
| | from 0.2 to 0.6 wt %; or |
| | from 0.2 to 0.5 wt %; or |
| | from 0.3 to 0.5 wt %. |
| from 0.08 to 2 wt % | from 0.01 to 10 wt %; or |
| | from 0.02 to 7 wt %; or |
| | from 0.03 to 5 wt %; or |
| | from 0.05 to 3 wt %; or |
| | from 0.08 to 2 wt %; or |
| | from 0.1 to 1 wt %; or |
| | from 0.2 to 0.8 wt %; or |
| | from 0.2 to 0.6 wt %; or |
| | from 0.2 to 0.5 wt %; or |
| | from 0.3 to 0.5 wt %. |
| from 0.1 to 1 wt % | from 0.01 to 10 wt %; or |
| | from 0.02 to 7 wt %; or |
| | from 0.03 to 5 wt %; or |
| | from 0.05 to 3 wt %; or |
| | from 0.08 to 2 wt %; or |
| | from 0.1 to 1 wt %; or |
| | from 0.2 to 0.8 wt %; or |
| | from 0.2 to 0.6 wt %; or |
| | from 0.2 to 0.5 wt %; or |
| | from 0.3 to 0.5 wt %. |
| from 0.2 to 0.8 wt % | from 0.01 to 10 wt %; or |
| | from 0.02 to 7 wt %; or |
| | from 0.03 to 5 wt %; or |
| | from 0.05 to 3 wt %; or |
| | from 0.08 to 2 wt %; or |
| | from 0.1 to 1 wt %; or |
| | from 0.2 to 0.8 wt %; or |
| | from 0.2 to 0.6 wt %; or |
| | from 0.2 to 0.5 wt %; or |
| | from 0.3 to 0.5 wt %. |
| from 0.2 to 0.6 wt % | from 0.01 to 10 wt %; or |
| | from 0.02 to 7 wt %; or |
| | from 0.03 to 5 wt %; or |
| | from 0.05 to 3 wt %; or |
| | from 0.08 to 2 wt %; or |
| | from 0.1 to 1 wt %; or |
| | from 0.2 to 0.8 wt %; or |
| | from 0.2 to 0.6 wt %; or |
| | from 0.2 to 0.5 wt %; or |
| | from 0.3 to 0.5 wt %. |
| from 0.2 to 0.5 wt % | from 0.01 to 10 wt %; or |
| | from 0.02 to 7 wt %; or |
| | from 0.03 to 5 wt %; or |
| | from 0.05 to 3 wt %; or |
| | from 0.08 to 2 wt %; or |
| | from 0.1 to 1 wt %; or |
| | from 0.2 to 0.8 wt %; or |
| | from 0.2 to 0.6 wt %; or |
| | from 0.2 to 0.5 wt %; or |
| | from 0.3 to 0.5 wt %. |

-continued

| xanthan gum | methyl cellulose |
|---|---|
| based on weight of the composition | |
| from 0.3 to 0.5 wt %. | from 0.01 to 10 wt %; or |
| | from 0.02 to 7 wt %; or |
| | from 0.03 to 5 wt %; or |
| | from 0.05 to 3 wt %; or |
| | from 0.08 to 2 wt %; or |
| | from 0.1 to 1 wt %; or |
| | from 0.2 to 0.8 wt %; or |
| | from 0.2 to 0.6 wt %; or |
| | from 0.2 to 0.5 wt %; or |
| | from 0.3 to 0.5 wt %. |

A highly preferred composition comprises
(i) a mixed metal compound containing at least one trivalent metal selected from iron (III) and aluminium and at least one divalent metal selected from of magnesium, iron, zinc, calcium, lanthanum and cerium,
(ii) xanthan gum in an amount of from 0.3 to 0.5 wt % based on the total composition
(iii) locust bean gum in an amount of from 0.3 to 0.5 wt % based on the total composition;
wherein the composition has been irradiated with ionising radiation in an amount of at least 4 kGy, such as from 4 to 10 kGy, such as at least 6 kGy, or such as from 6 to 10 kGy.

The present composition may contain one or more further components. In one preferred aspect, the composition is a pharmaceutical composition and further comprises (iv) one or more pharmaceutically acceptable adjuvants, excipients, diluents or carriers.

In one preferred aspect the composition is substantially free of a wetting agent. Many insoluble drugs require wetting agents, e.g. to disperse the drug, or antifoaming agents, to prevent the inclusion of air bubbles in the formulation. We have found the mixed metal compound when incorporated in the present composition does not require a wetting agent. This effect and the exclusion of a wetting agent is particularly pronounced when the mixed metal compound has a magnesium iron ratio between 1.5 and 2.5 and contains carbonate anions. By "substantially free of a wetting agent" it is meant the composition contains wetting agents in an amount of no greater than 10 wt %, preferably in an amount of no greater than 1 wt %, preferably in an amount of no greater than 0.5 wt %, preferably in an amount of no greater than 0.3 wt %, preferably in an amount of no greater than 0.22 wt %, preferably in an amount of no greater than 0.1 wt %, preferably in an amount of no greater than 0.05 wt %, preferably in an amount of no greater than 0.02 wt %, preferably in an amount of no greater than 0.01 wt %, preferably in an amount of no greater than 0.005 wt %, preferably in an amount of no greater than 0.001 wt %, preferably in an amount of no greater than 0.0001 wt %, preferably in an amount which is not measurable based on weight of the composition.

Another aspect to the invention is the combination of excipients has the effect of preventing any sensation of 'grittiness', due to the mixed metal compound component, in the mouth.

Optionally, the palatability of the formulation may be improved by the addition of sweeteners (either alone or in combination with sorbitol) and/or flavourings. For example, sweeteners such as Acesulfame K/Aspartame, Xylitol, Thaumatin (Talin) and Saccharin; and flavourings such as Butterscotch, Caramel, Vanilla, Mild peppermint and Strawberry, may be used.

Packaging

We have found that sachets are a convenient form of container for single dose formulations with the further advantage that we have selected packaging material that can withstand irradiation. Preferably sachets are selected which are suitable for single use only to avoid the need for prolonged in use microbial stability formulations; this because the use of preservatives are prohibitive in combinations with mixed metal compounds. We have therefore developed formulations which have to meet all the requirements mentioned hereinbefore as well as providing compatibility for use in sachets (i.e. pourability, homogeneity etc). Alternatively, the raw materials may be irradiated, however sources of microbial and bacterial contamination must be eliminated from the subsequent formulation make up and packaging stages to ensure sterility. This route is therefore less preferred.

The formulations are typically irradiated within 5 days after preparation of the formulation, preferably within 2 days, more preferably within 1 day even more preferably immediately after preparation of the formulation. It will be appreciated to one skilled in the art that initial microbial and fungal content of the raw materials and the cleanliness of the formulation preparation (i.e. prior to irradiation) is such as to minimise microbial and fungal contamination.

Polymers for use in packaging, such as sachets, which show tolerance to irradiation include polystyrene, polyethylene, polyesters, polysulfone, polycarbonates, polyurethane, PVC, Silicone, Nylon, Polypropylene (irradiation grades) and Fluoroplastics.

Where metallic foils are used as materials of construction for sachets, care must be taken when selecting materials to avoid e.g. leaching into or reaction with the sachet contents or should be coated with a suitable polymer to avoid leaching.

Uses

As described herein, in one aspect the present invention provides the composition for use in the treatment of hyperphosphataemia. However, the composition is not limited to this particular use. The composition may be used in accordance with the teachings of WO2009/016349 as an antacid.

Further Preferred Aspects and Advantages

A number of formulations each containing mixed metal compound have been identified, which deliver phosphate binding performance in a liquid dose form both initially and on storage, are of the appropriate microbiological quality, are physically stable and are of suitable appearance. The phosphate binding performance of the mixed metal compound is not inhibited by the excipients and other additives used in the formulations.

The first of these is formulation (see E24 below), based on an optimum combination of xanthan gum (0.35% w/v) and locust bean gum (0.35% w/v) which is preserved by irradiation at an optimum dose level (6 kGy). The formulation is preferred, having a good combination of physical and microbiological stability and phosphate binding efficacy/stability and suitable for use in sachets. It is particularly suitable for single use formulations where prolonged in use stability is not required.

A second formulation (see E22 below) based on a combination of PVP (0.5% w/v) and xanthan gum (1.0% w/v) has been found which is preserved by irradiation at a dose level (8 kGy). The formulation is preferred, having good physical and microbiological stability and phosphate binding efficacy/stability. It is particularly suitable for single use formulations where prolonged in use stability is not required.

A third formulation (see E10 below) based on a combination of methyl cellulose with xanthan gum has been found which is preserved by irradiation at a dose level (10 kGy). This formulation has storage stability (physical, microbiological and phosphate binding efficacy/stability). The formulation shows some reduction in phosphate binding performance which occurs during accelerated storage stability testing. It is particularly suitable for single use formulations where prolonged in use stability is not required.

We have found that sachets are a convenient form of container for single dose formulations with the further advantage that the packaging material can be selected to withstand irradiation.

The present invention will now be described in further detail by way of example only with reference to the accompanying figures in which:—

Figure 2:
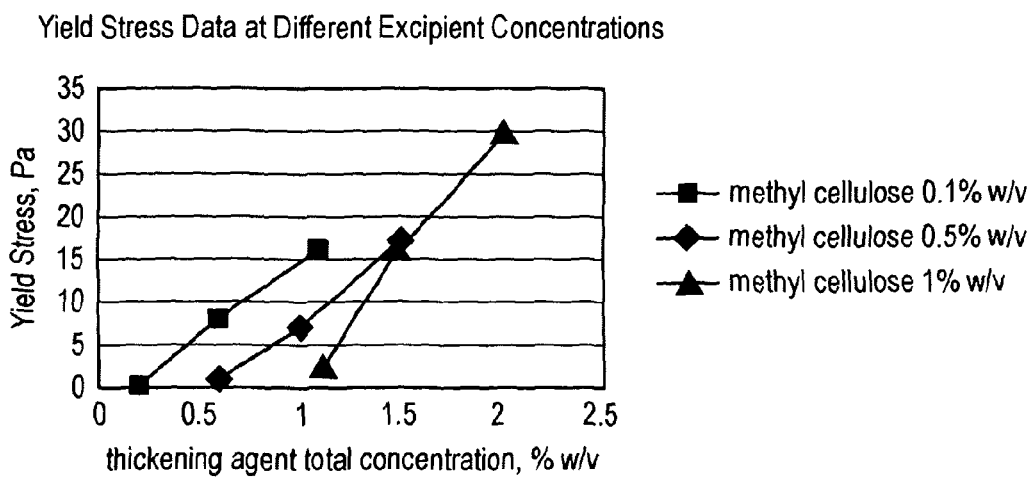

FIG. 1 shows a graph; and
FIG. 2 shows a graph.

The present invention will now be described in further detail in the following examples.

Rheology

Formulations with a yield stress have the theoretical ability to suspend solids within the formulation indefinitely. There was therefore a need to determine a minimum yield stress.

The theoretical minimum yield value (Pa) (calculated according to Method 2) to suspend the mixed metal compound was 0.2 Pa. Thickening agents were selected at a concentration which would provide a yield stress above the minimum critical value to prevent gravity-induced settling. The rheology of aqueous systems was then further assessed according to Method 3.

Because the formulation must be able to be handled during manufacture and poured and/or squeezed from a container during use, the yield value must not be more than 19 Pa Of course, if the formulation is to be squeezed from a sachet, for example, higher yield stress values might be acceptable but are preferably limited to less than 30 Pa (to maintain patient palatability and or texture).

The formulation must be easy to mix, pour or squeeze and swallow, whilst maintaining the mixed metal compound in suspension and stable upon storage. Consequently there is a need for a formulation that is of low viscosity at high shear and of high viscosity at low shear.

Thus an optimum range of yield stress and a low viscosity at high shear and of high viscosity at low shear exists. An optimum yield stress from 0.5 to approximately 19 Pa was identified experimentally, using a gravimetric settling test to establish the minimum yield value, and a visual assessment of 'pourability' which was found to determine the maximum yield stress.

No Excipient (Control)

A mixture of the micronised mixed metal compound in water (5% w/v mixed metal compound) was prepared, however the mixed metal compound settled out rapidly and the yield stress was less than 0.5 Pa. Thus the criterion of a physically stable formulation was not met.

Single Materials

Alginate (Comparative)

Mixtures of micronised mixed metal compound (5% w/v) with alginic acid (sodium, from brown algae, 3,500 cp for a 2% solution), (1 and 2% w/v, respectively) and water were prepared, the mixed metal compound settled rapidly even in the presence of relatively high concentrations of alginate. The formulations had no measurable yield stress and thus the criterion of a physically stable formulation was not met.

Carbopol 974 P NF (Comparative)

Carbomer 974 P NF is a polyacrylic acid which requires neutralisation of the acid functional group using a base to produce negatively charged carboxylate groups. This causes the polymer to uncoil and hence thicken aqueous systems.

A mixture of micronised mixed metal compound (5% w/v) with Carbopol 974 P NF (0.2% w/v) and water was prepared. The phosphate binding performance of the formulation is acceptable, the combination of mixed metal compound with Carbopol caused the system to 'gel' and it could no longer be poured.

Microcrystalline Cellulose (Comparative)

A mixture of micronised mixed metal compound (5% w/v) with microcrystalline cellulose 2% w/v) and water was prepared, again the mixed metal compound settled rapidly. Thus the criterion of a physically stable formulation was not met.

Methyl Cellulose (Comparative)

Mixtures of micronised mixed metal compound (5% w/v) with methyl cellulose (2 and 3% w/v, 400 cP grade; and 1%, 1500 cP grade, respectively) and water were prepared, again the mixed metal compound settled rapidly. Thus the criterion of a physically stable formulation was not met.

Colloidal Silica (Comparative)

Colloidal silicas, such as Aerosil 200 (supplier: Evonik) are commonly used to help structure liquid suspensions. Because of the small particle size and other particle characteristics colloidal silica has the ability to form a three-dimensional network in liquid systems. Colloidal silica can be effectively used to modify the rheology of compositions. However, it was found that the combination of colloidal silica and mixed metal compound, at a concentration of 0.5 and 10% w/v, respectively, failed to produce a physically stable formulation (settles within 24 hours).

Xanthan Gum (Comparative)

Mixtures of mixed metal compound (5% w/v) with various concentrations of xanthan gum (between 0.2 and 1% w/v, respectively) and water were prepared. Whilst each of the formulations displayed an improved stability (attributable in part to a measurable yield stress of between 1 and 10 Pa), visible floccules of mixed metal compound were observed. This was deemed to be unacceptable. The formation of floccules is not generally consistent with a formulation having good physical stability.

Summary

In summary, of the single excipients tested none provided yield stress suitable for suspension of the mixed metal compound Combinations of More than One Material In an attempt to solve the problem of visible floccules and optimising the preferred yield stress, various excipients were combined and tested at a range of concentrations. The composition of these formulations is given below in Tables 1, 2 and 3, below.

Xanthan Gum and Silica (Comparative)

Three different concentrations of colloidal silica were tested with three different concentrations of xanthan gum producing a matrix of nine formulations. The rheology and physical stability of the formulations were measured, and a qualitative assessment of the formulation appearance was made. Data are presented for the optimum formulation E1.

It was found that not all combinations of silica and xanthan gum produced stable formulations. We found, surprisingly that only those where silica is present in the approximate range of 0.1 to 0.5% w/v and xanthan gum 0.5 to 1.0% w/v and the sum of those agents is between approximately 0.5 and 1.0% w/v were suitable (Formulation E1).

The inclusion of colloidal silica did not significantly modify the preferential rheology of the formulation i.e. the advantageous yield stress and shear thinning properties of the formulation were maintained. Contrary to the prior art there was no requirement for inclusion of wetting or anti-foaming agents for proper dispersal of the mixed metal compound.

Our data demonstrates that contrary to the art, most combinations of xanthan gum and silica produce unstable suspensions of pharmaceuticals containing insoluble products. We discovered a suitable but narrow range which was stable prior to irradiation (i.e. E1 formulation) however upon irradiation silica formulations were found to only provide sterile formulation when irradiated at very high levels (more than 10 kGy) this in turn led to a decrease of the physical stability of the liquid (without being bound by theory it is believed that this is due to changes in the excipients).

TABLE 1

Summary of Formulation E1

|  | Composition, % w/v E1 |
| --- | --- |
| Fermagate (mixed metal compound) | 10 |
| Colloidal Silica | 0.5 |
| Xanthan Gum | 0.5 |
| Sorbitol | 6 |
| Sum thickening agents | 1.0 |
| Rheology |  |
| Yield stress (Pa), Method 3 | 7 |
| Physical stability |  |
| vol % sediment, Method 6 | 0 |
| vol % sediment, Method 7 | 37.5 |

Microcrystalline Cellulose and Sodium Carboxymethylcellulose (Comparative) and Xanthan Gum and Locust Bean Gum Avicel RC 591 is a water dispersible hydrocolloid used in the preparation of pharmaceutical suspensions and emulsions. It is a spray dried blend of microcrystalline cellulose and sodium carboxymethylcellulose. Data in respect of this product is reported as Formulation E2 below.

Avicel CL 611 is also blend of microcrystalline cellulose and sodium carboxymethylcellulose, however it is more suitable for storage as a dry formulation whereby liquid is added only at the point of use.

TABLE 2 formulations based on Avicel.

|  | Composition, % w/v | | | |
| --- | --- | --- | --- | --- |
|  | E2 | E3 | E4 | E5 |
| Fermagate (mixed metal compound) | 10 | 10 | 10 | 10 |
| Avicel RC 591 | 1.5 | 1.5 | 1.3 |  |
| Avicel CL 611 |  |  | 0.3 | 1.3 |
| Xanthan Gum |  |  |  | 0.3 |
| LBG |  |  |  | 0.02 |
| Sorbitol |  | 6 |  |  |
| Sum thickening agents | 1.5 | 1.5 | 1.6 | 1.62 |
| Rheology |  |  |  |  |
| Yield stress (Pa), Method 3 |  |  |  |  |
| Yield stress (Pa), Method 15 | 0.1 | ND | 5.5 | 4.5 |
| 'Pourability', Method 4 |  |  |  |  |
| Physical stability |  |  |  |  |
| Gravimetric test, Method 5 | (1) | ND | ND | ND |
| vol % supernat't, Method 18 | 65 | ND | 0 | 0 |
| Appearance |  |  |  |  |
| Observation |  |  |  | Little/no flocc |

ND = No Data
(1). Forms small layer of supernatant liquor upon storage

Formulation E2 containing Avicel RC 591 was found to produce an acceptable formulation but had a higher degree of separation when compared to E4 and E5. Formulation E3 was not physically stable and could therefore not be assessed. This may have been a consequence of limitations of the method of formulation make up.

Formulations E4 and E5 were developed with an optimised range of excipient combinations such as to provide physical stability, Surprisingly we found that the addition of a small quantity of Locust Bean Gum (i.e. formulation E5) provided a formulation which was suitable for storage as a liquid, contrary to its typical usage.

Xanthan Gum and Methyl Cellulose

Table 3 presents formulations E6 to E14 which are all based on combinations of methyl cellulose and xanthan gum at different concentrations.

Three different concentrations of methyl cellulose were tested with three different concentrations of xanthan gum producing a matrix of nine formulations. The rheology and physical stability of the formulations were measured, and a qualitative assessment of the formulation appearance was made.

TABLE 3

Summary of Formulations, Formulations E6 to E14

|  | E6 | E7 | E8 | E9 | E10 | E11 | E12 | E13 | E14 |
| --- | --- | --- | --- | --- | --- | --- | --- | --- | --- |
| Composition, % w/v |  |  |  |  |  |  |  |  |  |
| Fermagate (mixed metal compound) | 10 | 10 | 10 | 10 | 10 | 10 | 10 | 10 | 10 |

TABLE 3-continued

Summary of Formulations, Formulations E6 to E14

|  | E6 | E7 | E8 | E9 | E10 | E11 | E12 | E13 | E14 |
|---|---|---|---|---|---|---|---|---|---|
| Methyl cellulose | 0.1 | 0.5 | 1 | 0.1 | 0.5 | 1 | 0.1 | 0.5 | 1 |
| Xanthan gum | 0.1 | 0.1 | 0.1 | 0.5 | 0.5 | 0.5 | 1 | 1 | 1 |
| Sorbitol | 6 | 6 | 6 | 6 | 6 | 6 | 6 | 6 | 6 |
| Sum thickening agents | 0.2 | 0.6 | 1.1 | 0.6 | 1 | 1.5 | 1.1 | 1.5 | 2 |
| Rheology |  |  |  |  |  |  |  |  |  |
| Yield stress (Pa), Method 3 | 0.4 | 0.8 | 2.6 | 8 | 7 | 16.3 | 16.3 | 17 | 30 |
| 'Pourability', Method 4 |  |  |  |  |  |  |  |  | very thick |
| Physical stability |  |  |  |  |  |  |  |  |  |
| Gravimetric test, Method 5 | Note 1 |  |  |  |  |  |  |  |  |
| Vol % sediment, Method 6 | 34.4 | 12.5 | 12.5 | 0 | 0 |  | 0 | 0 |  |
| vol % sediment, Method 7 |  |  |  | 31.3 | <6.3 | <6.3 |  | <6.3 | <6.3 |
| Appearance |  |  |  |  |  |  |  |  |  |
| Observation 1 |  |  | Aearated |  |  | Aearated | some flocculation | some flocculation | minor flocculation |
| Observation 2 |  | bottom 12.5% darker | bottom 12.5% darker |  |  |  |  |  | Aearated |

Note 1 Full separation in 24 h

From Table 3 and FIGS. 1 and 2 it can be seen that the optimum range of methyl cellulose is between 0.5 and 1.0% w/v. This produces a physically stable formulation, with absence of aeration and absence of visible flocculation.

From the data it is seen that excessive sedimentation (Method 5) occurs at yield stress values up to 2.6 Pa. Even at higher yield stress values (8 Pa) sedimentation may still occur (Method 6) if the sum thickening agent value is not maintained at above 0.6% w/v.

Pourability is acceptable at yield stress values of up to 17 Pa, but is poor at values of 30 Pa.

Furthermore, excess amounts (above 1% w/v) of methyl cellulose were found to hinder Pi binding.

The inclusion of methyl cellulose can prevent the appearance of flocculation but that flocculation may still occur in formulations containing 1% w/v xanthan gum.

It was found that some combinations of methyl cellulose and xanthan gum were more preferred. Accelerated settling tests on formulations (all with 6% w/v sorbitol, 10% w/v Fermagate mixed metal compound) containing xanthan gum at 0.1% w/v and methyl cellulose at 0.1, 0.5 and 1% w/v respectively produced an excessive sediment volume (defined as being more than 10% v/v) in each case. Formulations combining xanthan gum at 1% w/v with methyl cellulose at 0.1, 0.5 and 1% w/v all showed some degree of flocculation and in some cases were difficult to pour (corresponding to a yield stress of around 19 Pa). Accelerated settling tests on the formulation containing 0.5% w/v xanthan gum and 0.1% w/v methyl cellulose produced an excessive sediment volume, whereas the formulation containing 0.5% w/v xanthan gum and 1% w/v methyl cellulose was excessively aerated during preparation. Furthermore the latter formulation had the same sediment volume as the optimum 0.5% w/v xanthan gum/0.5% w/v methyl cellulose formulation, with the disadvantage of higher overall suspending agent content.

The data (of Table 3) demonstrates the advantages of methyl cellulose over the use of silica as a thickening or "liquid structuring" agent preventing flocculation. Contrary to the use of silica, we found that methyl cellulose was not affected by irradiation.

Contrary to the teachings of the prior art (Adams et al 1972) we did not observe loss of gel structure in methyl cellulose following irradiation of liquids containing mixed metal compounds and Xanthan gum under the preferred formulations discussed herein below.

Furthermore, phosphate (Pi) binding was initially not affected by the presence of methylcellulose. Upon storage there was some inhibition of Pi binding in the presence of methyl cellulose but we found that this could be controlled by maintaining suitable lower levels of methyl cellulose (such as from 0.5 to 1% w/v). The selection of lower levels of methyl cellulose also maintained the required yield stress (2.6-19 Pa) and did not increase the potential for flocculation or settling. The viscosity of the formulation was such as to enable mixing, pouring or squeezing from the sachet and allow swallowing with no grittiness in mouth. There is especially a need for a formulation that is of low viscosity at high shear and of high viscosity at low shear and does not have loss of gel structure following irradiation.

Consequently, the use of methylcellulose provides advantages, such as providing a physically stable formulation, for liquids containing mixed metal compounds and Xanthan gum.

In preferred aspects the following conditions are maintained:
  sum thickening agents is maintained at above 0.6% w/v
  methyl cellulose concentration is limited to less than 1% w/v and more preferably from 0.5 to 1% w/v.
  xanthan gum concentration limited to less than 1% w/v
  Yield stress should be limited to between 2.6 Pa and 30 Pa. Furthermore, if the sum thickening agents is below 0.6% w/v, the minimum yield stress to prevent sedimentation is 8 Pa.

It was found that the inclusion of methyl cellulose in a formulation containing xanthan gum at certain preferred ratios of xanthan to methyl cellulose also prevented the formation of visible floccules of mixed metal compound.

Thus formulation E10 is preferred (high mixed metal compound concentration, yield stress in optimal range, shear thinning properties enabling re-dispersion of settled component, absence of visible floccules, physically stable under accelerated centrifugation test). Again, the advantageous rheology of the formulation was maintained and there was no requirement for inclusion of wetting agents or antifoaming agents for proper dispersal of the mixed metal compound.

Xanthan Gum and Polyvinyl Pyrrolidone (PVP)

Table 4 presents formulations E15 to E23 which are all based on combinations of PVP (polyvinyl pyrrolidone) and xanthan gum at different concentrations.

showed some degree of settling. In summary, Table 3 demonstrates that the most stable formulations are obtained where Xanthan gum and PVP are at a level from 0.5 to 1. Most stable formulation (E22) is obtained at levels of Xanthan gum and PVP at respectively 1 and 0.5% w/v and the yield stress is from 10 to 20 Pa, more preferably 15 Pa. Thus formulation E22 is preferred as this provides a high mixed metal compound concentration of 10% w/v, yield

TABLE 4

Summary of Formulations, Formulations E15 to E23

|  | E15 | E16 | E17 | E18 | E19 | E20 | E21 | E22 | E23 |
| --- | --- | --- | --- | --- | --- | --- | --- | --- | --- |
| Composition, % w/v | | | | | | | | | |
| Fermagate (mixed metal compound) | 10 | 10 | 10 | 10 | 10 | 10 | 10 | 10 | 10 |
| PVP | 0.1 | 0.5 | 1 | 0.1 | 0.5 | 1 | 0.1 | 0.5 | 1 |
| Xanthan gum | 0.1 | 0.1 | 0.1 | 0.5 | 0.5 | 0.5 | 1 | 1 | 1 |
| sorbitol | 6 | 6 | 6 | 6 | 6 | 6 | 6 | 6 | 6 |
| Sum thickening agents | 0.2 | 0.6 | 1.1 | 0.6 | 1 | 1.5 | 1.1 | 1.5 | 2 |
| Rheology | | | | | | | | | |
| Yield stress (Pa), Method 3 | 0.4 | 0.4 | 0.45 | 6.4 | 6.25 | 9 | 16 | 15 | 18.8 |
| 'Pourability', Method 4 | | | | | | | | | |
| Physical stability | | | | | | | | | |
| Gravimetric test, Method 5 | | | | | | | | | |
| vol % sediment, Method 6 | 18.8 | 18.8 | 18.8 | 0.0 | 0.0 | 0.0 | 0.0 | 0.0 | 0.0 |
| vol % sediment, Method 7 | 18.8 | 25.0 | 25.0 | 12.5 | 12.5 | 12.5 | 12.5 | 1.3 | 12.5 |
| vol % supernat't, Method 6 | | | | | | | | | |
| vol % supernat't, Method 7 | | | | | | | | | |
| Appearance | | | | | | | | | |
| Observation | | | | | | | | | | Flocs |

Note (1).
Forms small layer of supernatant liquor upon storage

Formulations E15 to E23 (Table 4)

It was found, surprisingly, that the combination of PVP when prepared in combination with Xanthan gum prevented the formation of visible floccules of mixed metal compound. For example, the physical stability upon storage (Accelerated settling test Method 6 and 7) was improved by maintaining dose levels of Xanthan gum and PVP at dose levels of from 0.5 to 1% w/v. Accelerated settling tests on the formulations (all with 6% w/v sorbitol, 10% w/v mixed metal compound) containing xanthan gum at 0.1% w/v and PVP at 0.1, 0.5 and 1% w/v, respectively and with xanthan gum at 0.5% and PVP at 0.1, 0.5 and 1% w/v, respectively produced an sediment volume in all cases. Of the remaining formulations, the formulation combining xanthan gum at 1% w/v with PVP at 1% w/v was gel like, and formulation E21 stress in a preferred range of from 10 to 20 Pa, shear thinning properties enabling re-dispersion of settled component, absence of visible floccules, physically stable under accelerated centrifugation test methods 6 and 7. Again, the advantageous rheology of the formulation was maintained and there was no requirement for inclusion of wetting agents or anti-foaming agents for proper dispersal of the mixed metal compound.

Xanthan Gum and Locust Bean Gum

Table 5 presents formulations E5 to E30 wherein PVP has been replaced by Locust Bean Gum (LBG) which are all based on combinations of Locust Bean Gum and xanthan gum at different concentrations. Formulation E5 additionally contains Avicel CL 611.

TABLE 5

Summary of Formulations E5 to E30

|  | E5 | E24 | E25 | E26 | E27 | E28 | E29 | E30 |
| --- | --- | --- | --- | --- | --- | --- | --- | --- |
| Composition, % w/v | | | | | | | | |
| Fermagate (mixed metal compound) | 10 | 10 | 10 | 10 | 10 | 10 | 10 | 10 |
| Avicel CL 611 | 1.3 | | | | | | | |
| LBG | 0.02 | 0.35 | 0.1 | 0.5 | 1 | 0.1 | 0.5 | 0.1 |
| Xanthan gum | 0.3 | 0.35 | 0.1 | 0.1 | 0.1 | 0.5 | 0.5 | 1 |
| sorbitol | | | 6 | 6 | 6 | 6 | 6 | 6 |
| Sum thickening agents, % w/v | 1.62 | 0.7 | 0.2 | 0.6 | 1.1 | 0.6 | 1 | 1.1 |

TABLE 5-continued

Summary of Formulations E5 to E30

|  | E5 | E24 | E25 | E26 | E27 | E28 | E29 | E30 |
|---|---|---|---|---|---|---|---|---|
| Rheology |  |  |  |  |  |  |  |  |
| Yield stress (Pa), Method 3 |  |  | 0 | 5.5 | 2.5 | ND | ND | ND |
| 'Pourability', Method 4 |  |  | Very runny | Thick but flows well | Thicker than 0.5/0.1 (LBG/XG), flows well | Thick jelly | Thick jelly | Thick jelly |
| Yield Stress (Pa), Method 15 | 4.5 | 7 |  |  |  |  |  |  |
| Physical stability |  |  |  |  |  |  |  |  |
| Gravimetric test, Method 5 |  |  | Separates quickly | ND | ND | ND | ND | ND |
| vol % sediment, Method 6 |  |  | 60.0 | 0 | 0 | ND | ND | ND |
| vol % sediment, Method 7 |  |  | 24.0 | 20 | 0 | ND | ND | ND |
| vol % supernat't, Method 6 |  |  | 0 | 0 | 0 | ND | ND | ND |
| vol % supernat't, Method 7 |  |  | 68 | 0 | 0 | ND | ND | ND |
| vol % supernat't, Method 18 | 0 | 0 | ND | ND | ND | ND | ND | ND |
| Appearance |  |  |  |  |  |  |  |  |
| Observation 1 | Little/no flocc | Little/no flocc | Flocculates | Little/no flocc | Little/no flocc | Little/no flocc | Little/no flocc | Little/no flocc |

From the data it is seen that excessive sedimentation (Method 7) occurs at yield stress values below 2.5 Pa (method 3 data).

Pourability is acceptable at yield stress values of up to 5.5 (method 3), but is poor at values of 19 Pa and above.

The inclusion of PVP can prevent the appearance of flocculation but that flocculation may still occur where the sum thickening agent concentration is up to 0.2% w/v.

Thus an optimum formulation exists:

sum thickening agents is maintained above 0.2% w/v.

yield stress limited to more than 5.5 Pa and up to 19 Pa

It was found, surprisingly, that the combination of Locust Bean Gum and xanthan gum as formulations E26 to E30 produced suspensions with no visible floccules of mixed metal compound. Formulation E25 wherein both xanthan gum and Locust Bean Gum were 0.1% w/v did flocculate. Formulation E28, E29 and E30 had the appearance of a thick jelly whereas E26 and E27 also had the appearance of the thick jelly but had good pourability. Thus the physical form of formulations E26 and E27 was found to be preferred where the xanthan gum was formulated at only 0.1% w/v. Results of the settling test were good for each. Based on the results for E26 and E27 a formulation consisting of 0.35% w/v xanthan gum and 0.35% w/v locust bean gum was ultimately selected to take forward, this is denoted formulation E24. This shared the advantageous physical form and absence of floccules of E26 and E27.

Irradiation Study

A number of preferred formulations were irradiated (parameters of investigation included physical properties, phosphate binding and microbiological stability). Formulations are listed in Table 6, below.

TABLE 6

Physical Stability of mixed metal compound Formulations

| | Formulation | | | | | |
|---|---|---|---|---|---|---|
| | E1 | E10 | E22 | E3 | E5 | E24 |
| Composition (% w/v) | | | | | | |
| Fermagate (mixed metal compound) | 10 | 10 | 10 | 10 | 10 | 10 |
| Colloidal Silica | 0.5 | | | | | |
| Xanthan gum | 0.5 | 0.5 | 1.0 | | 0.3 | 0.35 |
| Methyl Cellulose | | 0.5 | | | | |
| Kollidon CL M (PVP) | | | 0.5 | | | |
| Avicel RC 591 | | | | 1.5 | | |
| Avicel CL 611 | | | | | 1.3 | |
| Locust Bean Gum | | | | | 0.02 | 0.35 |
| Sorbitol 70% solution | 6 | 6 | 6 | 6 | 6 | 6 |
| Water | QS | QS | QS | QS | QS | QS |
| Absence of floccules | Yes | Yes | Yes | Yes | Yes | Yes |
| Rheology | | | | | | |
| Yield stress (Method 3, Pa) | 7 | 7 | 9 | ND | ND | ND |
| Yield stress (Method 15, Pa) | | | | | 4.5 | 7 |
| Physical stability | | | | | | |
| Vol % sediment (accelerated test, Method 6) | 0 | 0 | 0 | ND | ND | ND |
| Vol % sediment (accelerated test, Method 7) | 37.5 | <6.3 | 12.5 | ND | ND | ND |

In summary we developed suitable formulations of combinations of component (i) the mixed metal compound, component (ii) xanthan gum (from 0.1 to 1.0% w/v), component (iii) selected from one of (or combinations) of colloidal silica (Aerosil 200), methyl cellulose, blend of microcrystalline cellulose and sodium carboxymethylcellulose (Avicel RC 591 & CL 611 grades), PVP (Kollidon CL M) and Locust Bean Gum (from 0.1 to 1% w/v) and component (iv) sweetening agent selected as sorbitol (6%, preferred range 3 to 12%).

The main function of component (i) the mixed metal compound is that it provides phosphate binding capacity as well as functioning as a wetting agent.

The function of component (ii) the xanthan gum is its ability to produce a large increase in the viscosity of the liquid and to impart a yield stress upon the formulation. The viscosity of xanthan gum solutions decreases significantly with higher shear rates. This provides a suitable formulation for filling into sachets, in that the xanthan gum is thick enough at rest within the sachet to maintain homogeneity. However, the shear forces generated by e.g. filling, handling and squeezing, thins the formulation, so that the formulation can be easily dosed into the sachet and readily be dispensed from it.

The function of component (iii) is to prevent flocculation and settling. To prevent flocculation and settling after irradiation we found that polyvinyl pyrrolidone, locust bean gum and methyl cellulose are preferred.

Component (iv) was selected as a sugar substitute as low calorific value sweeteners and is preferred for subjects who may consume the composition for a prolonged period of time.

The above combinations of excipients and mixed metal compound at preferred concentration ranges have been found to meet the requirement of not significantly hindering phosphate binding, providing stable formulations upon storage (stable rheology, phosphate binding and sterility), preventing any sensation of 'grittiness' due to the mixed metal compound component in the mouth and being compatible with sterilisation treatment by irradiation and providing appropriate rheology to enable use in sachets.

Preservation by Irradiation Sterilisation

A study was carried out to identify the optimum gamma irradiation dose level for formulations described in Table 7.

The physical and chemical properties of each formulation were then tested at the following time points:—
1) Initial analysis after the manufacture of each batch.
2) Post irradiation: All formulations were irradiated at an average dose of 10 kGy.
3) Storage Stability: All formulations were stressed at 60° C. for one week after being irradiated. This was to help identify any likely degradation which may be seen in the long term stability study at less onerous conditions.

In order to meet the conflicting requirements of microbiological stability, physical stability and phosphate binding stability, an optimum irradiation dose level should be defined. Formulations were therefore irradiated at three radiation intensity levels, 6, 8, and 10 kGy. The characterisation data for the 18 systems is summarised below in Tables 8 and 9:

Excipients and mixed metal compound substance were taken from a single batch of material.

TABLE 7

| Component (iii) | Method | E1 | E10 0.5% w/v Methyl cellulose | E22 0.5% w/v PVP | E3 0.5% w/v Avicel | E4 1.3% w/v Avicel RC591 | E5 1.3% w/v Avicel CL611 | E24 0.35% w/v Locust Bean Gum |
|---|---|---|---|---|---|---|---|---|
| Results for Irradiation Study - Physical Property Results | | | | | | | | |
| Rheology | | | | | | | | |
| Yield Stress, Pa | 15 | | | | | | | |
| Irradiation, 0 kGy | | 6 | 7 | 17.5 | 0.1 | 5.5 | 4.5 | 7 |
| 6 kGy | | ND | 0 | 10.5 | 0.2 | 3.5 | 4 | 7 |
| 8 kGy | | ND | 0 | 8 | 0.2 | 1.4 | 3 | 6 |
| 10 kGy | | 4 | 0 | 7 | 0.15 | 1.75 | 1.25 | 5 |
| Phase Angle Delta, ° | 16 | | | | | | | |
| Irradiation, 0 kGy | | 31.3 | 21.6 | 16.2 | 34.8 | 26.2 | 22.2 | 14.0 |
| 6 kGy | | ND | 30.0 | 37.3 | 43.1 | 43.9 | 37.4 | 12.1 |
| 8 kGy | | ND | 28.2 | 47.3 | 32.0 | 38.1 | 35.5 | 12.2 |
| 10 kGy | | 48.75 | 30.8 | 50.6 | 18.3 | 39.7 | 32.0 | 14.8 |
| Storage stability, 6 kGy | | ND | 34.4 | 45.2 | 24.3 | 30.9 | 26.4 | 10.6 |
| 8 kGy | | ND | 56.0 | 56.7 | 23.7 | 34.9 | 22.1 | 14.8 |
| 10 kGy | | 80.64 | 56.5 | 65.1 | 38.9 | 56.1 | 26.4 | 22.4 |
| Complex Viscosity, Pa · s | 17 | | | | | | | |
| Irradiation, 0 kGy | | 0.95 | 2.6 | 5.6 | 0.1 | 1.8 | 1.8 | 3.6 |
| 6 kGy | | ND | 2.2 | 2.0 | 0.1 | 0.6 | 0.9 | 4.1 |
| 8 kGy | | ND | 1.0 | 1.2 | 0.2 | 0.4 | 0.6 | 3.7 |
| 10 kGy | | 0.49 | 1.0 | 1.0 | 0.3 | 0.5 | 0.6 | 2.5 |
| Storage stability, 6 kGy | | ND | 2.2 | 1.5 | 0.3 | 1.0 | 2.0 | 5.0 |
| 8 kGy | | ND | 0.2 | 0.9 | 0.3 | 0.7 | 1.1 | 2.0 |
| 10 kGy | | 0.09 | 0.2 | 0.5 | 0.3 | 0.3 | 3.3 | 1.0 |
| Physical Stability (vol % supernatant) | 18 | | | | | | | |
| Irradiation, 0 kGy | | 2 | 0* | 0.5 | 65 | 0 | 0 | 0 |
| 6 kGy | | ND | 0* | 0 | 65 | 10 | 4.9 | 0 |
| 8 kGy | | ND | 0* | 0 | 65.9 | 41.5 | 12.2 | 0 |
| 10 kGy | | 2 | 10.8 | 4.9 | 67.5 | 40 | 15 | 0 |
| Storage stability, 6 kGy | | ND | 5 | 0 | 65 | 37.5 | 27.5 | 0 |
| 8 kGy | | ND | 7.5 | 5 | 66.7 | 47.6 | 42.5 | 0 |
| 10 kGy | | 16 | 4.9 | 4.9 | 70.7 | 57.5 | 50 | 0 |
| Diffraction line half width, °2 theta | 14 | | | | | | | |
| | | | 1.02 | | 0.76 | | | |
| Irradiation 0 kGy | | 0.93 | 0.83 | | 0.81 | | | |
| 10 kGy | | 0.83 | 0.81 | | 0.8 | | | |

TABLE 7-continued

| Component (iii) | Method | E1 | E10 0.5% w/v Methyl cellulose | E22 0.5% w/v PVP | E3 0.5% w/v Avicel | E4 1.3% w/v Avicel RC591 | E5 1.3% w/v Avicel CL611 | E24 0.35% w/v Locust Bean Gum |
|---|---|---|---|---|---|---|---|---|
| Storage stability | 10 kGy | 0.80 | | | | | | |
| pH | 11 | | | | | | | |
| Irradiation | 0 kGy | 8.6 | | | | | | |
| | 10 kGy | 8.2 | 9.2 | | 9.2 | | | |
| Storage stability | 10 kGy | 8.2 | 9 | | 9.1 | | | |
| 0 kGy sample, after 7 weeks storage | | 7.9 | 9 ND | | 9.1 ND | | | |
| Results for Irradiation Study - Micro and Efficacy Results | | | | | | | | |
| Microbiology, cfu/ml | 12 | | | | | | | |
| Irradiation, | 0 kGy | 680 000 | ND | ND | ND | ND | ND | ND |
| | 6 kGy | ND | 0 | 20 | 0 | 0 | 5175 | 0 |
| | 8 kGy | ND | 80 | 0 | 0 | 0 | 680 | 0 |
| | 10 kGy | >680 000 | 0 | 0 | 0 | 0 | 0 | 0 |
| P-binding, mmol/gAPI | 13 | | | | | | | |
| Irradiation, | 0 kGy | 0.56 | 0.64 | 0.66 | 0.75 | 0.65 | 0.64 | 0.66 |
| | 6 kGy | ND | 0.67 | 0.67 | 0.66 | 0.65 | 0.64 | 0.66 |
| | 8 kGy | ND | 0.65 | 0.67 | 0.67 | 0.64 | 0.64 | 0.66 |
| | 10 kGy | 0.61 | 0.64 | 0.66 | 0.75 | 0.65 | 0.64 | 0.66 |
| P-binding (storage stability), mmol/g API | 13 | | | | | | | |
| Storage stability testing at 40° C./75% RH, 1 mnth | | ND | ND | ND | ND | ND | ND | ND |
| Storage stability | 6 kGy | ND | 0.61 | 0.64 | 0.6 | 0.6 | 0.6 | 0.6 |
| | 8 kGy | ND | | | | | | |
| | 10 kGy | 0.56 | 0.52 | 0.63 | 0.61 | 0.58 | 0.59 | 0.62 |
| | | | 0.48 | 0.56 | 0.66 | 0.59 | 0.58 | 0.61 |

ND No data

Conclusion

Physical Stability

An absence of flocculation is best achieved by use of two excipients in combination, as previously described.

In the centrifugal separation test (indicator to determine the potential for settling) of formulation E1, less than 2% of separation occurred in samples tested immediately after manufacture and post irradiation; and increased to 16% after storage stability testing.

For formulation E10 less than 2% of separation occurred in samples tested immediately after manufacture and post irradiation; and increased to only 9% after storage stability testing.

For formulation E3 at all stages. The percentage for the solid layer fluctuates due to the formulation not being homogenous to start with. In the gravimetric separation test, after 30 minutes a clear layer of separation was observed for initial, post irradiation and after storage stability testing samples.

The preferred value for supernatant (% basis) is zero, this indicates no separation under the accelerated separation test. Samples E22 and E24 perform best according to this test.

Particle Size

We have found that an optimum particle size exists from 1 to 30 micron for the mixed metal compound. If the particle size is too large, the yield stress required to suspend the particle will be too high and subsequently the handling characteristics of the formulation will not be optimal. For example, it may become too difficult to pour the formulation from a bottle, or squeeze it from a sachet. Additionally at a particle size of above about 200 micron, P-binding is reduced. Furthermore, above a particle size of approximately 30 micron, a 'gritty' mouth feel may be found. The optimum particle size of the excipients (i.e. components ii and iii) were selected such as to be very similar (i.e. less than 30 micron) to that of the mixed metal compound to maintain homogeneity of the slurry.

Viscosity

The Viscous or loss modulus is a measure of the liquid like behaviour of the formulation.

The phase angle, δ, is calculated from the Elastic and Viscous modulus and is a measure of the gel strength, where $$\tan \delta = G''/G'$$

If δ<45° then the material is a gel and the lower the phase angle the stronger the gel. The Elastic modulus is a measure of the solid like behaviour of the formulation.

The Elastic modulus and the Viscous modulus were highest for initial E1 samples tested post manufacture; however they decreased following irradiation, and then decreased further following storage stability testing. The phase angle increased from an initial value of 31.3° to 48.75° post irradiation and 80.64° after storage stability testing. This suggests the formulation became more liquid in behaviour primarily following storage and irradiation did not contribute significantly. The yield stress decreased from approximately 6 to approximately 4 Pa following irradiation but this surprisingly did not lead to an increase in flocculation (settling).

The Elastic modulus and the Viscous modulus were highest for initial E10 samples tested post manufacture; however they decreased following irradiation, and then decreased further following storage stability testing. The phase angle increased from an initial value of 16.57° to 44.30° post irradiation and 49.24° after storage stability testing. This suggests the formulation became more liquid in behaviour primarily following irradiation and storage did not contribute significantly; however, these properties were found to maintain their suitability for use in sachets. The yield stress decreased from approximately 12.5 to approximately 6 Pa following irradiation but this surprisingly did not lead to an increase in flocculation.

No rheology was performed on formulation E3 because it formed an unstable suspension. Because the formulation is fast settling, sample heterogeneity is an issue, giving highly variable results.

Irradiation

From the separation data (Table 7) it is seen that the response to irradiation and storage differs between formulations. Formulations E10, E22 and E24 all show physical stability, as demonstrated by the values of supernatant test, value of yield stress and absence of flocculation whereas comparative formulations E3 and E4 do not.

E2 and E4 comprise Avicel and the data shows that these formulation are not stable. E10 comprises methyl cellulose and xanthan gum whereas E2 and E4 consisting of Avicel (which in turn is a mixture methyl cellulose and carboxymethyl) are not stable during irradiation.

The corresponding preferred yield stress range as defined in Method 3 is about 7 to 17.5 Pa for pre-irradiation samples and about 5 to 10.5 Pa for post irradiation samples (depending upon the exact irradiation dose applied). For pre-irradiated samples the preferred range for phase angle, Delta, is about 14 to 16°. Again for pre-irradiated samples the preferred complex viscosity range is about 3 to 6 Pa s.

Phosphate Binding

From Table 7 it can be seen that across samples, irradiation does not affect phosphate binding. On accelerated storage stability testing for material of examples E4 to E24 there is a slight decrease in phosphate binding however this is wholly consistent with the decline seen on storage of the 2:1 ratio mixed metal compound, prepared according to the method of WO 1999/015189. For samples E10 and E22, the change is small at 6 kGy but is more pronounced at 8 kGy, therefore it is important to select the lowest irradiation that maintains the preferred microbiological and physical stability. Phosphate binding of formulations E1 and E10 were not significantly reduced by the effect of irradiation.

The initial E3 sample showed slightly high phosphate binding, this may be due to sample heterogeneity (fast settling sample). The irradiated and irradiated and accelerated storage stability tested sample displayed more typical phosphate binding performance.

Hydrotalcite Structure of Mixed Metal Compound (XRD Analysis)

Diffraction Line Half Width of E1 and E10 were not significantly influenced by irradiation and after storage stability testing treatment.

XRD's did not show any appearance of additional new crystalline phases (such as spinell) originating from a breakdown or change of the hydrotalcite structure when irradiated at the preferred radiation dosage.

Sterility (Microbiology)

From the microbiological data (Table 7) it is seen that a varying quantity of irradiation is required to ensure sterility. For example, for formulation E22, the optimum irradiation dose is 8 kGy, whereas for formulation E24 the optimum irradiation dose is 6 kGy.

For formulation E1 the microbiological results showed that the formulation was not sterile post irradiation, the only way to make the formulation sterile would be to increase the irradiation dosage to greater than 10 kGy. It is very likely that this will further decrease the physical properties of the formulation and exacerbate the separation problem. Irradiation is therefore not considered a suitable method for preserving this formulation. The total micro organism count for samples tested after manufacture was 680,000 cfu/1 ml of sample and was shown to spread post irradiation. All organisms were visually identified as *Bacillus* spp (Predominant types: Gram negative bacilli). This indicates that irradiation of the formulation was not successful in the presence of the silica.

For formulation E10 the total micro organism count for samples tested after manufacture was 450,000 cfu/1 ml of sample. Post irradiation samples were shown to be sterile i.e. zero organism count. All organisms were visually identified as *Bacillus* spp (Predominant types: Gram negative *bacilli*). The microbiological results for formulation E10 showed the formulation was sterile post irradiation.

No total micro organism count was performed on E3 samples taken post manufacture; however the sample was shown to be sterile post irradiation.

Packaging

Suitable packaging forms may include sachets, bottles and food.

Thus an optimum combination of mixed metal compound, excipients and irradiation dose to produce efficacious, sterile formulation with acceptable formulation characteristics (palatability, grittiness) and packaging (sachets and bottles) has been identified whilst maintaining good P-binding (both initial and on storage), physical stability and microbiological count.

Summary

The results clearly showed a decrease in the physical properties of formulations E1 and E10 both post irradiation and after storage stability testing. However, E10 was sterile whereas E1 was found not to be.

Surprisingly, we found that to improve the stability of E10 it would be feasible to use a lower irradiation dose. A lower dose may still preserve the formulation but the irradiation would have a reduced effect on the physical properties of the formulation.

Formulation E3 was not physically stable, even prior to irradiation, and could therefore not be assessed. This may have been a consequence of limitations of the method of formulation make up.

Table 7 demonstrates that the preferred formulations which can be sterilised are those that comprise combinations of xanthan gum with one of PVP, LBG, methyl cellulose preferably selected from a preferred dose range. Although combinations of xanthan gum and colloidal silica or Avicel were found to prevent flocculation and sedimentation, upon irradiation, decomposition was observed.

4 kGy Irradiation Study

The composition of the formulations tested are given below.

|  | Formulation | | |
| --- | --- | --- | --- |
| Raw Material | 31 % w/v | 32 % w/v | 33 % w/v |
| Fermagate (Mixed Metal Compound) | 10 | 10 | 10 |
| Sorbitol 70% solution | 6 | 6 | 6 |
| Xanthan gum | 0.5 | 0.35 | 1.0 |
| Methyl cellulose | 0.5 | — | — |
| Locust bean gum | — | 0.35 | — |
| PVP (Kollidon CL M) | — | — | 0.5 |

Each formulation was manufactured on a 3.5 liter scale and packed into 125 ml translucent HDPE bottles.

The physical and chemical properties of each formulation were then tested at the following time points:—
1) Initial analysis after the manufacture of each batch.
2) Post irradiation: All formulations were irradiated at an average dose of 4 kGy; this was achieved by cycling between 3.6 and 4.4 kGy.

Four 125 ml bottles were available for testing at each stage of analysis.

Microbial analysis was performed by Isotron to determine bioburden count pre and post irradiation.

All 3 formulations were tested pre and post irradiation in respect of
- appearance, pH and density
- rheology (Method 15 and 16)
- rotational viscosity (Method 17)
- kinematic viscosity (Method 21)
- centrifugal separation (Method 18)
- gravitational separation (Method 22)
- Microbiology (Method 12)

Results

|  |  | Time point | |
| --- | --- | --- | --- |
| Test | Units | Initial | Irradiated |
| Appearance |  | a | a |
| pH |  | 9.2 | 9.0 |
| Density | g/ml | 1.08 | 1.11 |
| Rotational viscosity | cP | 2706 | 1433 |
| Kinematic viscosity | seconds | 32 | 13 |
| Centrifugal separation | % supernatant | 0 | 0 |
| Gravimetric separation | % supernatant | 0 | 0 |
| Elastic modulus G' | Pa | 20.7 | 11.6 |
| Viscous modulus G" | Pa | 7.7 | 5.8 |
| Phase angle δ | ° | 20.3 | 26.4 |
| Complex viscosity | Pa · s | 3.4 | 2.0 | a = A rusty orange/brown colour with an aerated top layer.

Appearance, pH and Density
Formulation 31
  A rusty orange brown coloured suspension with an aerated top layer after manufacture there was no change in appearance post irradiation.
  The pH was 9.2 at manufacture and 9.0 post irradiation.
  The density was 1.08 g/ml at manufacture and 1.11 g/ml post irradiation.
Formulation 32
  A rusty orange brown coloured suspension after manufacture there was no change in appearance post irradiation.
  The pH was 9.2 at manufacture and 9.1 post irradiation.
  The density was 1.12 g/ml at manufacture and 1.12 g/ml post irradiation.
Formulation 33
  A rusty orange brown coloured suspension after manufacture there was no change in appearance post irradiation.
  The pH was 9.2 at manufacture and 9.0 post irradiation.
  The density was 1.12 g/ml at manufacture and 1.11 g/ml post irradiation
Rheology
Formulation 31
  The Elastic modulus and the Viscous modulus were highest for initial samples tested post manufacture; however they decreased following irradiation. The phase angle increased from an initial value of 20.3° to 26.4° post irradiation. This suggests the formulation became more liquid in behaviour following irradiation. A phase angle of greater than 45° is generally considered to be the transition between a gel and a liquid.
Formulation 32
  The Elastic modulus and the Viscous modulus were highest for initial samples tested post manufacture; however they decreased following irradiation. The phase angle had a very small decrease from an initial value of 12.5° to 12.0° post irradiation. This suggests the irradiation had very little effect on the gel properties of the formulation.
Formulation 33
  The Elastic modulus was highest for initial samples tested post manufacture; however decreased following irradiation. There was a very small increase in the Viscous modulus from manufacture to post irradiation. The phase angle increased from an initial value of 14.7° to 24.0° post irradiation. This suggests the formulation became more liquid in behaviour following irradiation.
Rotational Viscosity
Formulation 31
  The initial rotational viscosity was 2706 cPs, this was reduced to 1433 cPs after irradiation.
Formulation 32
  The initial rotational viscosity was 5756 cPs, this was reduced to 4729 cPs after irradiation.
Formulation 33
  The initial rotational viscosity was 6256 cPs, this was reduced to 4136 cPs after irradiation.
Kinematic Viscosity
Formulation 31
  The flow rate decreased from 32 seconds to 13 seconds for the formulation post irradiation for the first break in flow. At these time points 75 ml and 90 ml of sample had flowed through the orifice for post manufacture and post irradiated samples respectively.
Formulation 32
  No continuous flow was observed for the sample post manufacture or post irradiation.
  The formulation formed droplets, the times given in the data tables is the time for the first droplet to fall.
Formulation 33
  The flow rate decreased from 22 seconds to 21 seconds for the formulation post irradiation. At these time points 45 ml and 73 ml of sample had flowed through the orifice for post manufacture and post irradiated samples respectively.
Centrifugal Separation
  For each of Formulations 31, 32 and 33 no separation occurred in samples tested immediately after manufacture and post irradiation.
Gravimetric Separation
  For each of Formulations 31, 32 and 33 no separation occurred in samples tested immediately after manufacture and post irradiation.
Microbiology
Formulation 31
  The total micro organism count for samples tested after manufacture was 6,600 cfu/ml of sample. Three of the five samples tested showed CFU's. The predominant types were visually identified as *Bacillus* spp and *Staphylococcus* spp. Post irradiation samples were shown to have 21 cfu/ml of sample. One of the five samples tested showed CFU's. The predominant types were visually identified as *Staphylococcus* spp.
Formulation 32
  The total micro organism count for samples tested after manufacture was 30 cfu/ml of sample. One of the five samples tested showed CFU's. The predominant types were visually identified as *Bacillus* spp and *Staphylococcus* spp. Post irradiation samples were shown to have 0 cfu/ml of sample.

Formulation 33

The total micro organism count for samples tested after manufacture was 20 cfu/ml of sample. One of the five samples tested showed CFU's. The predominant types were visually identified as *Bacillus* spp and *Staphylococcus* spp. Post irradiation samples were shown to have 0 cfu/ml of sample.

Conclusion

Formulation 31

The results showed that following irradiation there was a change in the rheological properties of the formulation indicating it had become more liquid. This was consistent with what had been observed previously at higher irradiation doses; however, importantly these changes did not impact on the suspending properties of formulation 31. The suspending properties of formulation 31 were unaffected by irradiation, as were appearance, pH and density.

The microbiological results showed that the formulation was sterile post irradiation in four of the five samples tested.

Formulation 32

Formulation 2 was similar to Formulation 1 in that there were slight changes to its rheological character post-irradiation; however, these changes did not alter the suspending properties.

The microbiological results showed that Formulation 2 was sterile post irradiation in all samples.

Formulation 33

Following irradiation, Formulation 3 behaved in a similar manner to Formulation 2. A dose of 4 kGy was sufficient to sterilise the formulation and, despite slight changes in rheological properties, it did not separate and remained a physically stable suspension.

In summary, the irradiation of all tested formulations at 4 kGy resulted in a decrease in 1 to various rheological properties. This suggested the formulations became more liquid in character, however, despite these changes the suspending properties were unaffected at the current drug loading. Of the three formulations analysed, formulation 2 (xanthan gum/locust bean gum) and formulation 3 (xanthan gum/PVP) were shown to be sterile in all samples following irradiation at 4 kGy.

EXAMPLES

The mixed metal compound used in each of the examples of the present specification is Fermagate, available from INEOS Healthcare Ltd (UK). Fermagate is an iron magnesium hydroxy carbonate of the formula $[Mg_4Fe_2(OH)_{12}]\cdot CO_3\cdot 4H_2O$. The product is described in and may be prepared in accordance with the teachings of WO99/015189.

Formulation E1

To make 100 ml suspension:

To 6 g 70% sorbitol solution add 25 ml purified water. Whilst mixing, add 0.5 g colloidal silica and 10 g mixed metal compound. To this add sufficient water to make 50 ml suspension and mix well.

Warm (50° C.) 35 ml of water and whilst mixing add 0.5 g xanthan gum. Allow the solution to cool to room temperature and add sufficient water to make 50 ml solution. Mix well.

Add the solution to the suspension and mix well.

Formulation E2

Using Lightin stirrer and 5 liter beaker
1. To 2250 ml purified water add 56.25 g Avicel RC 591.
2. Mix to fully hydrate the Avicel
3. Whilst mixing add 375 g mixed metal compound.
4. Mix well
5. To this add sufficient water to make 3750 ml suspension and mix well.
6. Pour into bucket.

Formulation E3

Using Lightin stirrer and 5 liter beaker
1. To 2250 ml purified water add 56.25 g Avicel RC 591.
2. Mix to fully hydrate the Avicel
3. Whilst mixing add 225 g 70% sorbitol solution followed by 375 g mixed metal compound.
4. Mix well
5. To this add sufficient water to make 3750 ml suspension and mix well.
6. Pour into bucket.

Formulation E4

Using Lightin stirrer and 5 liter beaker
1. To 2250 ml purified water add 48.75 g Avicel RC 591.
2. Mix to fully hydrate the Avicel (approx 30 mins)
3. Add 11.25 g xanthan gum
4. Mix for 16 minutes
5. Whilst still mixing add 225 g 70% sorbitol solution followed by 375 g mixed metal compound.
6. Mix well
7. To this add sufficient water to make 3750 ml suspension and mix well.
8. Pour into bucket Formulation E5

1. To 2250 ml purified water add 48.75 g Avicel CL 611
2. Mix to fully hydrate the Avicel
3. Add 11.25 g xanthan gum and mix to fully hydrate
4. Add 0.75 g locust bean gum
5. Whilst mixing add 225 g 70% sorbitol solution followed by 375 g mixed metal compound.
6. Mix well
7. To this add sufficient water to make 3750 ml suspension and mix well.
8. Pour into bucket.

Formulation E10

Preparation of Suspension
Use Kitchen Aid Mixer
1. To 450 g 70% sorbitol solution add 1875 ml purified water.
2. Whilst mixing add 37.5 g methyl cellulose and 750 g mixed metal compound.
3. To this add sufficient water to make 3750 ml suspension and mix well.

Preparation of Solution Phase
Use Lightin Stirrer
1. Warm (50° C.) 2625 ml of water
2. Whilst mixing add 37.5 g xanthan gum mix well.
3. Allow the solution to cool to room temperature
4. Add sufficient water to make 3750 ml solution. Mix well.

Combination of Two Phases
1. Transfer solution phase into the suspension phase.
2. Mix well
3. Dispense into a labelled bottles.

Formulations E6 to E14

Formulations E6 to E14 were made in accordance with the method for E10 but with excipients in quantities described in Table 3.

Formulation E22
Preparation of Suspension
Use Kitchen Aid Mixer
1. To 1875 ml of purified water add 37.5 g Kollidon CLM.
2. Whilst mixing add 450 g of 70% sorbitol solution and 750 g mixed metal compound.
3. To this add sufficient water to make 3750 ml suspension and mix well.

Preparation of Solution Phase

Use Lightin Stirrer
1. Warm (50° C.) 2250 ml of water
2. Whilst mixing add 75 g xanthan gum and mix well.
3. Allow the solution to cool to room temperature
4. Add sufficient water to make 3750 ml solution. Mix well.
Combination of Two Phases
1. Transfer suspension phase into the solution phase.
2. Mix well
3. Dispense into a labelled bottles.
Formulations E15 to E23
Were made in accordance with the method for E22 but with excipients in quantities described in Table 3.
Formulation E24
1. To 1100 ml purified water add 13.125 g xanthan gum and mix to fully hydrate (=Phase A).
2. In a separate beaker add 13.125 g Locust bean gum to 1100 ml purified water and mix to fully hydrate (=Phase B).
3. Add phase B to phase A and mix well.
4. Add 225 g sorbitol solution followed by 375 g mixed metal compound and mix well.
5. To this add sufficient water to make 3750 ml suspension and mix well.
6. Pour into bucket
Formulations E25 to E30
were made in accordance with the method for E24 but with excipients in quantities described in Table 5.
Sachet Filling
Place a representative sample of the formulation into a sachet filling machine and pump the required quantity of sample into the selected sachet. Agitation of the formulation batch may be required. Heat seal the open end the sachet once filled.
Irradiation
Cobalt 60 is used as a source of gamma irradiation. The product to be irradiated are moved through the irradiation plant by a conveyor system in such a way as to ensure uniform irradiation of the product at the required irradiation intensity. In one particular irradiation system, the product can be placed inside a 'tote box' which is placed within the conveyor system. The absorption of irradiation by the product is measured indirectly using a dosimeter.
Methods
Method 1—Particle Size Analysis Mixed Metal Compound
The particle size was determined using a Mastersizer 'S' fitted with a 300 Rf lens and a DIF 2012 dispersion unit. The data was interpreted and analysed using Malvern Mastersizer software. The Malvern was connected to a process grade water supply. The following program parameters were used, 80% pump speed, 80% stirrer speed, 50% ultrasonic and 3 minute residence time. The background level was checked to be below 100 units. When prompted by the program the sample was added in portions to reach between 15%-25% obscuration. The analysis commenced automatically. The residual was checked to be less than 1%. The sample was analysed in duplicate. The results were calculated using the software by taking the % volume under the particle sizes between 1.85 and 184 microns. This was expressed as percentile results with the Average Particle Size (D50, $50^{th}$ percentile), $90^{th}$ Percentile (D90) and $10^{th}$ Percentile (D10).
Method 2—Calculation of Theoretical Fluid Yield Stress Required to Suspend Particle
For fluid systems containing particles, the yield stress of the fluid which is required to prevent sedimentation of those particles may be determined theoretically. The stress exerted by a spherical particle in dilute suspension is calculated using the following formula:

$$\sigma_s = rg(d-p)/3$$

Therefore, if the fluid has a yield stress exceeding $\sigma_s$ the suspended particles should in theory not settle out.
$\sigma_s$=yield stress, Pa
r=particle radius, m
g=acceleration due to gravity=9.81 m/s$^2$
d=particle density, kg/m$^3$
p=fluid density, kg/m$^3$
Method 3—Yield Stress Measurement
The sample shear stress was characterised at varying levels of shear rate using a Physica (Anton Paar) Rheolab MC1, with Z1 bob and MB-Z1/SM cup. From the shear stress and shear rate data the yield stress can be readily determined.
Method 4—Pourability
A qualitative assessment of the pourability ('runny', 'thick' etc.) of the liquid dose can be made by pouring the liquid from a suitable container e.g. a transparent bottle.
Method 5—Gravimetric Settling Test
Approximately 45 ml sample is homogenised, placed in a straight sided transparent container of 50 ml volume. The volume of sediment or supernatant is observed at specified time intervals and may be expressed as a % of the total sample volume.
Method 6—Accelerated Settling Test 1
A 40 ml sample was centrifuged using a Labofuge 400R centrifuge running at 500 rpm for 15 minutes. The degree of separation was then quantified by calculating the volume of sediment or supernatant as a percentage of the total sample volume.
Method 7—Accelerated Settling Test 2
A 40 ml sample was centrifuged using a Labofuge 400R centrifuge running at 2000 rpm for 15 minutes. The degree of separation was then quantified by calculating the volume of sediment or supernatant as a percentage of the total sample volume.
Method 8—Irradiation
500 ml sample stored in a plastic bottle was irradiated with gamma radiation at a dose level of between 6 and 10 kGy.
Method 9—Storage Stability Testing 1
500 ml of sample stored in a plastic bottle was placed in an oven at a temperature of 60° C. for one week. The sample was cooled to room temperature prior to testing.
Method 10—Storage Stability Testing 2
500 ml of sample stored in a plastic bottle was placed in an oven at a temperature of 50° C. for one week. The sample was cooled to room temperature prior to testing.
Method 11—pH
10 ml of sample was transferred to a sterilin jar and the pH measured whilst stirring using a calibrated pH meter.
Method 12—Microbiological Testing
The microbiological dose setting procedures, in accordance with recognised standards (BS EN 552/ISO11137, 'Sterilization of medical devices. Validation and routine control of sterilization by irradiation') require exposure of product to low, predetermined irradiation doses.

Method 13—Phosphate Binding 5 ml of sample was added to 7.5 ml of 67 mM phosphate solution maintained at 37° C., and agitated on an orbital shaker for 30 minutes. Slurry then filtered through 0.45 µm filter tip, and 1 ml of resultant filtrate diluted to 100 ml with AnalaR water. This solution was analysed on UV/Vis spectrophotometer using molybdovanadic colorimetric method at 375 nm.

Method 14—Diffraction Line Half Width

Liquid dose sample dried in an oven at 50° C. overnight. Dried sample milled via pestle and mortar and approx 2 g sent to LGC Runcorn for full scan powder x-ray diffraction. The powders were run as received in deep packed specimen holders, and data collected from 2-70 degrees 2 theta on a Philips PW1800 automatic powder x-ray diffractometer using copper k alpha radiation generated at 40 kV and 55 mM and a 4 second per point count time.

Method 15—Yield Stress Measurement

The sample shear stress was characterised at varying levels of shear rate using a Bohlin CVO controlled stress rheometer using cone and plate geometry (CP 4°/40 mm) 25° C. From the shear stress and shear rate data the yield stress can be readily determined.

Method 16—Phase Angle Measurement

The phase angle characterised using a Bohlin CVO controlled stress rheometer using cone and plate geometry (CP 4°/40 mm)@25° C.

Method 17—Complex Viscosity

The complex viscosity was characterised using a Brookfield LVDV-II+ viscometer, spindle 3 set at 12 rpm.

Method 18—Accelerated Separation Test 3

The sample was centrifuged using an accuSPIN 400 (Fisher) centrifuge running at 1000 rpm for 10 minutes. The degree of separation was then quantified by calculating the volume of sediment or supernatant as a percentage of the total sample volume.

Method 19—Phosphate Binding Test for Mixed Metal Compound

Phosphate Binding Capacity and Mg Release

Phosphate buffer (pH=4) was prepared by weighing 5.520 g (+/−0.001 g) of sodium di-hydrogen phosphate followed by addition of AnalaR™ water and transferring to a 1 ltr volumetric flask.

To the 1 ltr volumetric flask was then added 1 M HCl drop-wise to adjust the pH to pH 4 (+/−0.1) mixing between additions. The volume was then accurately made up to 1 ltr using AnalaR™ water and mixed thoroughly.

0.5 g (+/−0.005 g) of each sample was added to a volumetric flask (50 ml) containing 40 mM phosphate buffer solution (12.5 ml) at 37.5° C. in a Grant OLS 200 Orbital shaker. All samples were prepared in duplicate. The vessels were agitated in the orbital shaker for 30 minutes. The solution was then filtered using a 0.45 µm syringe filter. 2.5 ml aliquots of supernatant were pipetted of the supernatant and transferred into a fresh blood collection tubes. 7.5 ml of AnalaR™ water were pipetted to each 2.5 ml aliquot and the screw cap fitted and mixed thoroughly. The solutions were then analysed on a calibrated UV Vis.

The phosphate binding capacity was determined by:

Phosphate binding $(mmol/g) = S_P$ $(mmol/l) - T_P$ $(mmol/l)/W$ $(g/l)$ where:

$T_P$=Analyte value for phosphate in the phosphate solution after reaction with phosphate binder=solution P (mg/l)*4/30.97.

$S_P$=Analyte value for phosphate in the phosphate solution before reaction with phosphate binder.

W=concentration binder (g/l) used in test method (i.e. 0.4 g/10 ml=40 g/l)

Magnesium release was determined by:

Magnesium release $(mmol/g) = T_{Mg}$ $(mmol/l) - S_{Mg}$ $(mmol/l)/W$ $(g/l)$ where:

$T_{Mg}$=Analyte value for magnesium in the phosphate solution after reaction with phosphate binder=solution Mg (mg/l)*4/24.31.

$S_{Mg}$=Analyte value for magnesium in the phosphate solution before reaction with phosphate binder.

Method 20—Particle Density

Particle density can be derived by measuring the volume of liquid required to fill the inter-particle space within a sample of mixed metal compound of known mass and bulk volume. The particle volume is calculated by subtracting the liquid volume from the bulk volume. The particle density is calculated by dividing the original sample mass by the derived particle volume result. The mixed metal compound should be poorly soluble in the selected liquid.

Method 21—Kinematic Viscosity

The kinematic viscosity was determined using a Ford ASTM D1200 cup No 5. This is designed for flow times between 30 and 100 seconds, by allowing a known volume (100 ml) to flow through an orifice of specific dimensions.

Method 22—Gravitational Separation

The gravitational separation was assessed by monitoring 10 ml of sample in a measuring cylinder over a period of time. Any phase separation was noted and the volume of supernatant recorded.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry or related fields are intended to be within the scope of the following claims

The invention claimed is:

1. A composition comprising an aqueous suspension comprising:
   (i) an insoluble mixed metal compound capable of binding phosphate containing at least one trivalent metal selected from iron (III) and aluminium and at least one divalent metal selected from of magnesium, iron, zinc, calcium, lanthanum and cerium, wherein the component (i) is present in an amount up to 12% by weight, based on the total weight of the composition,
   (ii) xanthan gum present in the composition in an amount of no greater than about 2% by weight, based on the total weight of the composition;
   (iii) at least one of
      (a) polyvinyl pyrrolidone
      (b) locust bean gum
      (c) methyl cellulose wherein the composition has been irradiated with ionising radiation in an amount of at least 4 kGy.

2. A composition according to claim 1 where in the compound is of formula I $$M^{II}_{1-x}M^{III}_{x}(OH)_2 A^{n-}_{y} \cdot mH_2O \quad (I)$$

wherein $M^{II}$ is one or more bivalent metals and is at least $Mg^{2+}$;
$M^{III}$ is one or more trivalent metals and is at least $Fe^{3+}$;
$A^{n-}$ is one or more n-valent anions and is at least $CO_3^{2-}$;
$(\Sigma yn)/x$ is from 0.5 to 1.5
$0 < x \leq 0.4$,
$0 < y \leq 1$ and
$0 < m \leq 10$.

3. A composition according to claim 1 wherein the compound has an aluminium content of less than 10000 ppm.

4. A composition according to claim 1 wherein the composition has been irradiated with ionising radiation in an amount of at least 6 kGy.

5. A composition according to claim 1 wherein the composition has been irradiated with ionising radiation in an amount of at least 8 kGy.

6. A composition according to claim 1 wherein the composition has been irradiated with ionising radiation in an amount of at least 10 kGy.

7. A composition according to claim 1 wherein component (iii) is present in an amount of no greater than 2 wt % based on weight of the composition.

8. A composition according to claim 1 wherein the xanthan gum and component (iii) are present in a ratio of 2:1 to 1:2.

9. A composition according to claim 1 wherein the xanthan gum and component (iii) are present in a ratio of approximately 1:1.

10. A composition according to claim 1 wherein the composition comprises at least polyvinyl pyrrolidone.

11. A composition according to claim 10 wherein the composition comprises (ii) xanthan gum and (iii) polyvinyl pyrrolidone, wherein the xanthan gum and polyvinyl pyrrolidone are present in a ratio of approximately 2:1.

12. A composition according to claim 10 wherein the composition has been irradiated with ionising radiation in an amount of at least 8 kGy.

13. A composition according to claim 1 wherein the composition comprises at least locust bean gum.

14. A composition according to claim 13 wherein the composition comprises (ii) xanthan gum and (iii) locust bean gum, wherein the xanthan gum and locust bean gum are present in a ratio of approximately 1:1.

15. A composition according to claim 13 wherein the composition has been irradiated with ionising radiation in an amount of at least 6 kGy.

16. A composition according to claim 1 wherein the composition comprises at least methyl cellulose.

17. A composition according to claim 16 wherein the composition comprises (ii) xanthan gum and (iii) methyl cellulose, wherein the xanthan gum and methyl cellulose are present in a ratio of approximately 1:1.

18. A composition according to claim 16 wherein the composition has been irradiated with ionising radiation in an amount of at least 10 kGy.

19. A composition according to claim 1 wherein the composition is a pharmaceutical composition and optionally further comprises (iv) one or more pharmaceutically acceptable adjuvants, excipients, diluents or carriers.

20. A composition according to claim 1 for use as a medicament.

21. A pharmaceutical composition according to claim 1 for binding phosphate.

22. A pharmaceutical composition according to claim 1 for use in the treatment of hyperphosphataemia.

23. A composition comprising an aqueous suspension comprising:
(i) an insoluble mixed metal compound capable of binding phosphate containing at least one trivalent metal selected from iron (iii) and aluminum and at least one divalent metal selected from magnesium, iron, zinc, calcium, lanthanum, and cerium, wherein component (i) is present in the composition in an amount of about 8% to 12% by weight, based on the total weight of the composition,
(ii) xanthan gum, wherein component (ii) is present in the composition in an amount of no greater than about 2% by weight, based on the total weight of the composition, and
(iii) at least one of (a) polyvinyl pyrrolidone, (b) locust bean gum, and (c) methyl cellulose, wherein component (iii) is present in an amount no greater than about 2% by weight based on the total weight of the composition, wherein the composition has been irradiated with ionizing radiation in an amount of at least 4 kGy.

24. An aqueous suspension comprising:
(i) an insoluble mixed metal compound capable of binding phosphate containing at least one trivalent metal selected from iron (III) and aluminium and at least one divalent metal selected from magnesium, iron, zinc, calcium, lanthanum and cerium,
(ii) xanthan gum;
(iii) at least one of
(a) polyvinyl pyrrolidone
(b) locust bean gum
(c) methyl cellulose
wherein the xanthan gum and component (iii) are provided in a ratio of 2:1 to 1:2, the suspension has been irradiated with ionising radiation in an amount of at least 4 kGy, and the suspension has a yield stress of greater than about 2.6 Pa to about 19 Pa.

25. The aqueous suspension of claim 24, wherein the xanthan gum is present in the suspension in an amount of no greater than about 2% by weight, based on the total weight of the suspension.

26. The aqueous suspension of claim 25, wherein the mixed metal compound is present in the suspension in an amount up to about 12 wt %.

* * * * *